(12) United States Patent
Wang et al.

(10) Patent No.: US 10,730,845 B2
(45) Date of Patent: Aug. 4, 2020

(54) HEAT-RESISTANT POLYLACTIC ACID CONTINUOUSLY-EXTRUDED FOAMED MATERIAL AND PREPARATION METHOD THEREOF

(71) Applicant: NINGBO HOMELINK ECO-ITECH CO., LTD., Ningbo (CN)

(72) Inventors: Xiong Wang, Ningbo (CN); Peng Li, Ningbo (CN); Huxiao Chen, Ningbo (CN); Dan Lu, Ningbo (CN)

(73) Assignee: NINGBO HOMELINK ECO-ITECH CO., LTD., Ningbo (CN)

( * ) Notice: Subject to any disclaimer, the term of this patent is extended or adjusted under 35 U.S.C. 154(b) by 0 days.

(21) Appl. No.: 16/490,902

(22) PCT Filed: May 10, 2018

(86) PCT No.: PCT/CN2018/086269
§ 371 (c)(1),
(2) Date: Sep. 4, 2019

(87) PCT Pub. No.: WO2019/104946
PCT Pub. Date: Jun. 6, 2019

(65) Prior Publication Data
US 2020/0024243 A1  Jan. 23, 2020

(30) Foreign Application Priority Data
Dec. 1, 2017 (CN) .......................... 2017 1 1249187

(51) Int. Cl.
| | |
|---|---|
| *C07D 303/16* | (2006.01) |
| *C07D 301/03* | (2006.01) |
| *C08L 67/04* | (2006.01) |
| *C08K 5/11* | (2006.01) |
| *C08K 5/1515* | (2006.01) |
| *C08J 9/14* | (2006.01) |
| *C08K 3/34* | (2006.01) |

(52) U.S. Cl.
CPC ......... *C07D 303/16* (2013.01); *C07D 301/03* (2013.01); *C08J 9/142* (2013.01); *C08K 3/34* (2013.01); *C08K 5/11* (2013.01); *C08K 5/1515* (2013.01); *C08L 67/04* (2013.01)

(58) Field of Classification Search
CPC ...... C07D 303/16; C07D 301/03; C08J 9/142; C08L 67/04; C08K 5/11; C08K 5/1515
See application file for complete search history.

(56) References Cited

U.S. PATENT DOCUMENTS

| | | | |
|---|---|---|---|
| 8,586,658 B2 * | 11/2013 | Serizawa | C08F 289/00 524/210 |
| 2008/0262118 A1 | 10/2008 | Cink et al. | |
| 2009/0054559 A1 | 2/2009 | Serizawa et al. | |
| 2011/0263732 A1 | 10/2011 | Ramesh et al. | |

FOREIGN PATENT DOCUMENTS

| | | |
|---|---|---|
| CN | 102086299 A | 6/2011 |
| CN | 101362833 B | 8/2012 |
| CN | 102321269 B | 7/2013 |
| CN | 103232694 A | 8/2013 |
| CN | 103819885 A | 5/2014 |
| CN | 104140659 A | 11/2014 |
| CN | 105219044 A | 1/2016 |

OTHER PUBLICATIONS

Zhiyun Yang et al.,"Factors affecting cell structure of continuous extrusion foaming poly(lactic acid)(PLA)", Chemical Industry and Engineering Progress, 2014, vol. 33, Supplement 1, p. 233-237.
Yuwu Ma et al.,"Effect of Supercritical Carbon Dioxide on Extrusion Foaming for Pla", China Plastics, 2012, 26(12): 72-75.

* cited by examiner

*Primary Examiner* — Timothy R Rozof
(74) *Attorney, Agent, or Firm* — Bayramoglu Law Offices LLC

(57) ABSTRACT

An ethylene bis-12-hydroxystearamide grafted glycidyl citrate (EBH-g-ECA) and a preparation method thereof are provided; the EBH-g-ECA can be used as a multifunctional auxiliary agent in a polymer material, and particularly has a chain extension and a crystal nucleation effect in a polyester polymer material. A heat-resistant polylactic acid continuously-extruded foamed material containing EBH-g-ECA is further provided. The continuous foaming technology can be realized by using the heat-resistant polylactic acid foamed material, and the prepared foamed product has a high heat resistance, a uniform appearance, a low density, and complete biodegradation. A polylactic acid foamed material preparation method for a heat-resistant is provided, which is easy to be industrialized and has a great significance for realizing the large-scale replacement of petroleum-based plastic disposable foamed products such as PP and PS.

10 Claims, 5 Drawing Sheets

HEAT-RESISTANT POLYLACTIC ACID CONTINUOUSLY-EXTRUDED FOAMED MATERIAL AND PREPARATION METHOD THEREOF

CROSS REFERENCE TO THE RELATED APPLICATIONS

This application is the national phase entry of International Application No. PCT/CN2018/086269, filed on May 10, 2018, which is based upon and claims priority to Chinese Patent Application No. 201711249187.9, filed on Dec. 1, 2017, the entire contents of which are incorporated herein by reference.

TECHNICAL FIELD

The invention relates to the field of a green environmentally-friendly full biodegradable material and a preparation thereof, in particular to an ethylene bis-12-hydroxystearamide (EBH) grafted glycidyl citrate (ECA) and a heat-resistant polylactic acid continuously-extruded foamed material containing ethylene bis-12-hydroxystearamide grafted glycidyl citrate (EBH-g-ECA) and a preparation method thereof.

BACKGROUND

In recent years, the "oil shortage", "white pollution", "greenhouse effect" and "smog weather" caused by polymer materials have become increasingly severe, and bio-based degradable polymer materials have gradually attracted people's attention. Polylactic acid (PLA) is an environmentally friendly polymer material which is degradable and has similar mechanical properties to polystyrene and is considered to be the most industrialized.

However, a poor heat resistance and a high price have become key factors limiting the large-scale industrial application of polylactic acid. On the one hand, the heat distortion temperature of polylactic acid is only about 55° C., which greatly limits the practical use performance and transportation of polylactic acid products (the temperature inside the container in summer even reaches 70° C. or higher). On the other hand, the price of polylactic acid is still relatively high compared to petroleum-based plastics such as polypropylene and polystyrene. Polylactic acid foamed products can effectively reduce the density and reduce the weight of individual products, thus solving the problem of a high price.

The production methods of foamed materials mainly include continuous extrusion, autoclave, injection molding foaming, rapid pressure relief and rapid temperature rising. Continuous extrusion is popular for its high production efficiency; however, at present, polylactic acid foaming less relates to the use of continuous extrusion. This is because polylactic acid is a semi-crystalline polymer, which is slow in recrystallinity, and since the melt strength of the polylactic acid matrix is low and its processing window is narrow, the conventional continuous extrusion foaming technology and process are not suitable for the production of polylactic acid foamed materials.

In view of the above problems of polylactic acid foaming and low heat resistance, the existing improvements mainly include the addition of nanoparticles to improve the foaming performance, the use of a chain extender to increase the molecular weight and the nucleating agent to change the process conditions. These technical solutions can improve the foaming performance and heat resistance of the PLA to a certain extent, but basically have not left the laboratory.

For example, Chinese patents CN 101362833 B, CN 102321269 B and CN 104140659 A disclose batch foaming techniques such as polylactic acid molding foaming or reaction kettle, which have a complicated molding process and a long molding cycle and thus are not suitable for industrial production. CN 103819885 A discloses a polylactic acid foamed material and a preparation method thereof, but the advantages of bio-source and biodegradability of polylactic acid are greatly sacrificed with composite petroleum-based plastics such as polyethylene or polypropylene, and the oil dependence and white pollution hazards still cannot be completely solved. American Patents such as US 20080262118 and US 20110263732 relates to the preparation of polylactic acid foamed materials with composite D-type PLA, but the foam size is large, the opening ratio is high, the accuracy requirement for foaming process is high, the cost is high, and industrial production is difficult to achieve. The applicant's prior patent CN 105219044 A also discloses a heat-resistant polylactic acid material which incorporates a chain extender and a crystallization nucleating agent to improve the melt strength and heat resistance of the polylactic acid, respectively, but since the melt strength and crystallization rate are still not ideal, the size of the polylactic acid cells is large and the distribution is not uniform, which leads to the decrease of the mechanical properties of the final polylactic acid foamed material.

Although the heat-resistant polylactic acid foamed material has a broad application market in the fields of disposable lunch boxes, snack boxes and hamburger boxes, instant noodle bowls and packaging, so far, there is no fully satisfactory polylactic acid foamed product on the market; polylactic acid foamed materials are still in the theoretical research stage. Therefore, improving the heat resistance of polylactic acid foamed materials and achieving rapid and efficient industrial production are of a great significance for achieving large-scale replacement of petroleum-based foamed products.

SUMMARY

In order to solve the problem of continuous foaming and heat resistance of the heat-resistant polylactic acid in the prior art, the present invention synthesizes a series of polymers which function as both a chain extender and a crystallization nucleating agent in the polylactic acid foamed material.

It is an object of the present invention to provide a series of novel polymers as shown in Formula I, especially to provide ethylene bis-12-hydroxystearamide grafted glycidyl citrate (EBH-g-ECA) as shown in Ia.

A second object of the present invention is to provide a use of the above polymer as a chain extender and a crystallization nucleating agent in a polylactic acid foamed material.

A third object of the present invention is to provide a method for producing the above polymer.

A fourth object of the present invention is to provide a polylactic acid foamed material containing EBH-g-ECA, which has a high foaming ratio, a low density, a uniform appearance, a mild process, a simple preparation and full biodegradation.

It is still another object of the present invention to provide a method for producing the above polylactic acid foamed material.

The above object of the present invention is achieved by the following technical means:

The present invention provides a compound shown in Formula I having the structural Formula shown in Formula I:

Formula I

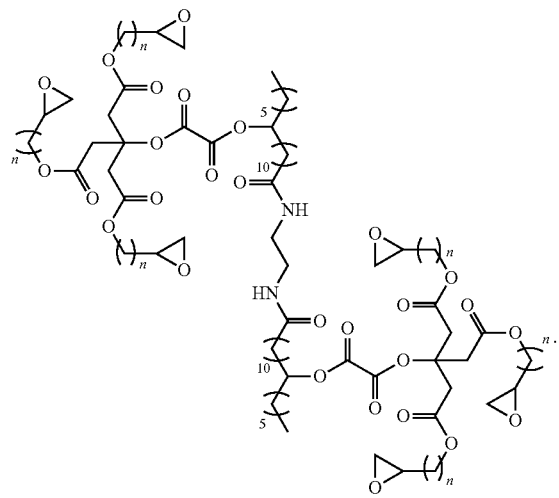

wherein n is an integer and $1 \leq n \leq 9$. As an exemplary embodiment, n is 1, in which case the compound shown in Formula I is ethylene bis-12-hydroxystearamide grafted glycidyl citrate (EBH-g-ECA), and the chemical Formula is $C_{82}H_{112}N_2O_{28}$; its corresponding structural Formula is as shown in Formula Ia.

Formula Ia

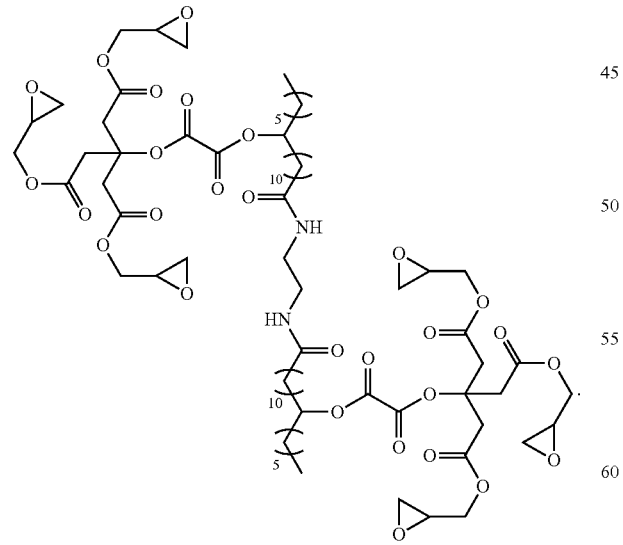

In another aspect, the invention provides the synthesis of an intermediate compound of Formula I, which has the structural Formula shown in Formula II:

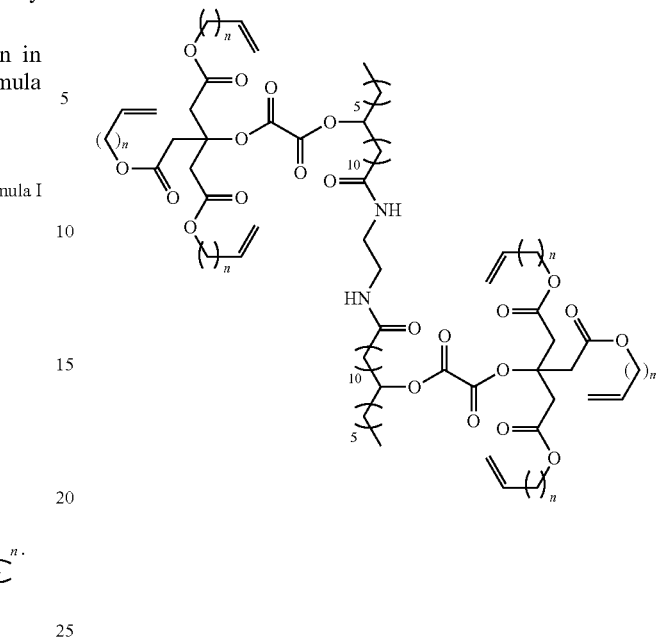

wherein n is an integer and $1 \leq n \leq 9$; as an exemplary embodiment, n is 1, in which case the Formula II is ethylene bis-12-hydroxystearamide grafted citric acid olefin ester (EBH-g-ECA), and the chemical Formula is $C_{82}H_{112}N_2O_{22}$; its corresponding structural Formula is as shown in Formula IIa.

Formula IIa

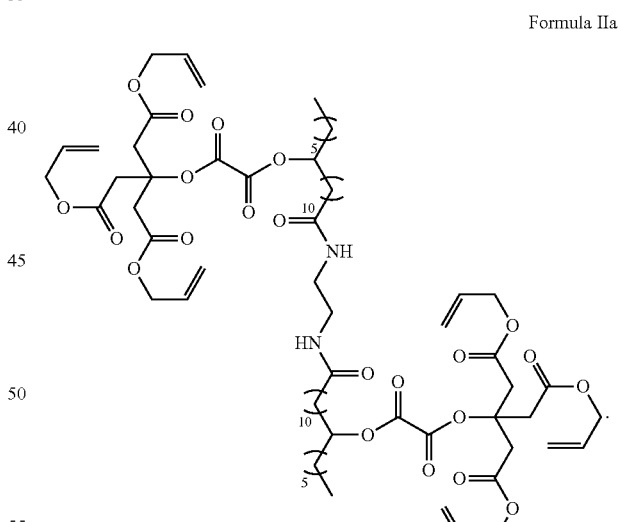

In another aspect, the invention provides the synthesis of an intermediate compound of Formula I, ethylene bis-12-hydroxystearamide grafted citric acid, which has the chemical Formula $C_{64}H_{88}N_2O_{22}$, and the structural Formula as shown in Formula III:

Formula III

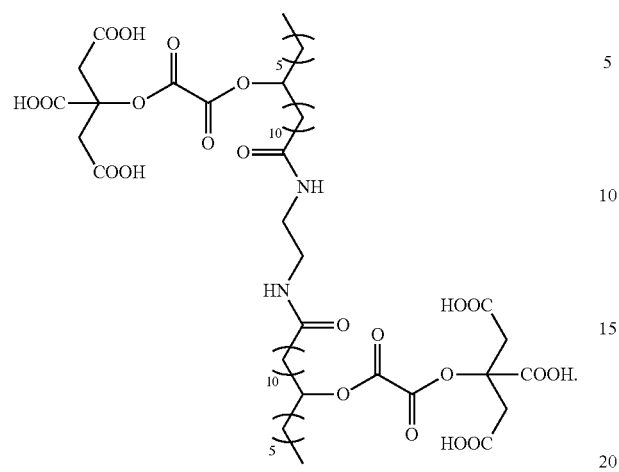

In another aspect, the invention also provides a method for preparing the above compound shown in Formula I comprising the steps of:

S1: subjecting citric acid, oxalyl chloride and ethylene bis-12-hydroxystearamide to an elimination reaction to obtain a Formula III: ethylene bis-12-hydroxystearamide grafted citric acid;

S2: subjecting Formula III obtained in step S1: ethylene bis-12-hydroxystearamide grafted citric acid and a halogenated olefin to an elimination reaction to obtain a compound shown in Formula II:

S3. subjecting the Formula II obtained in S2 to an oxidation reaction to obtain a compound shown in Formula I;

wherein n is an integer and $1 \leq n \leq 9$.

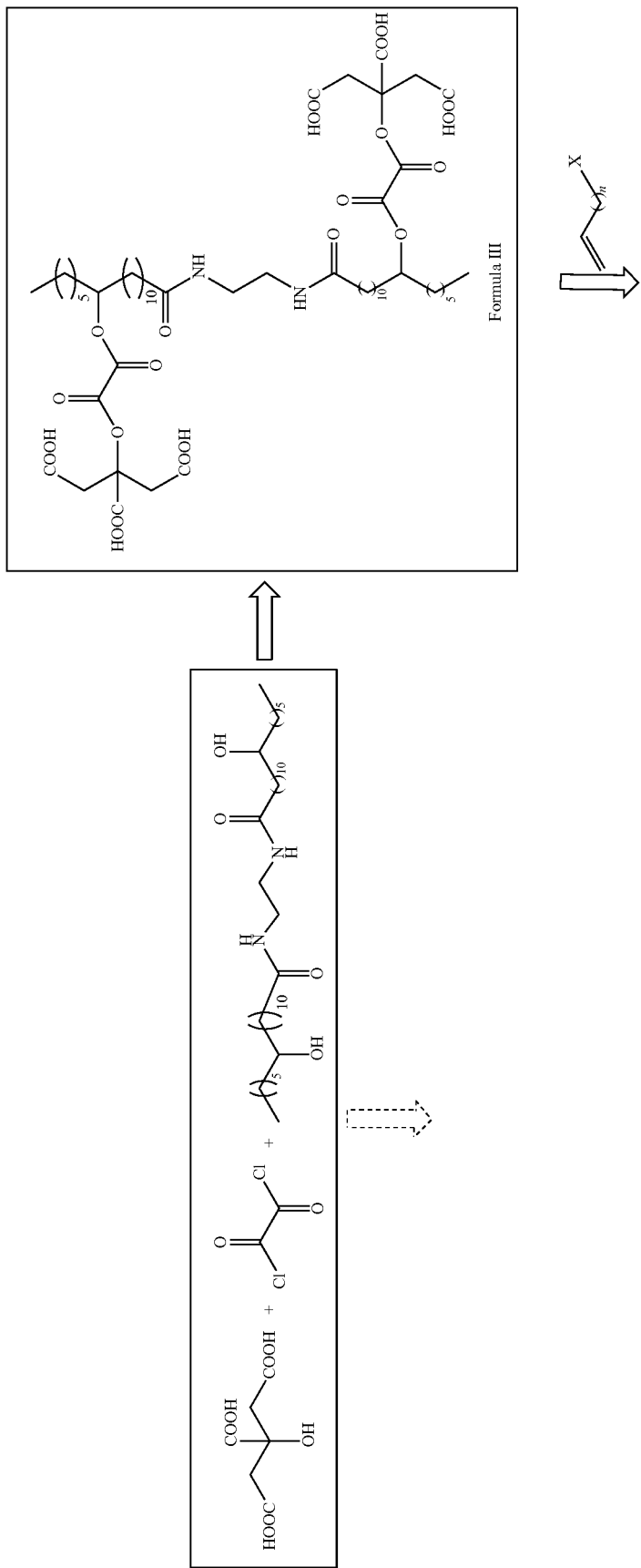

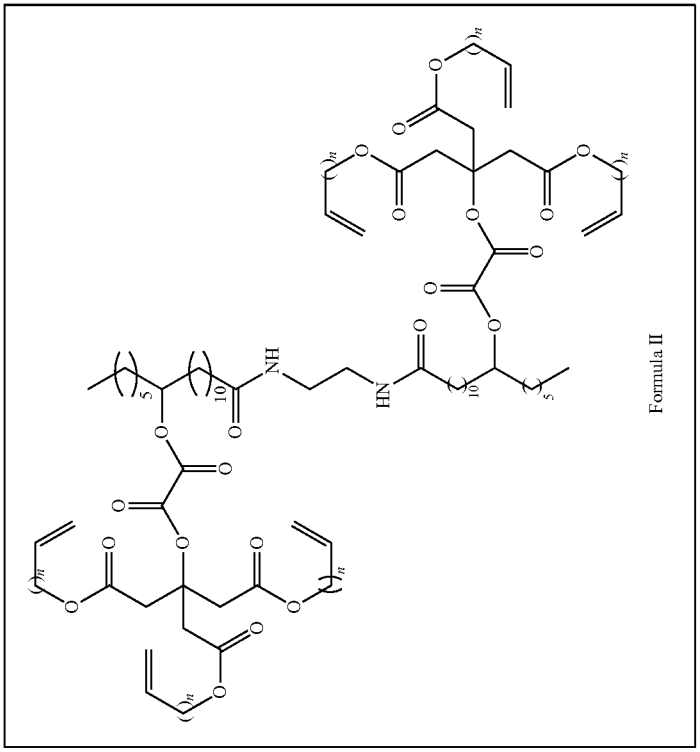
Formula II
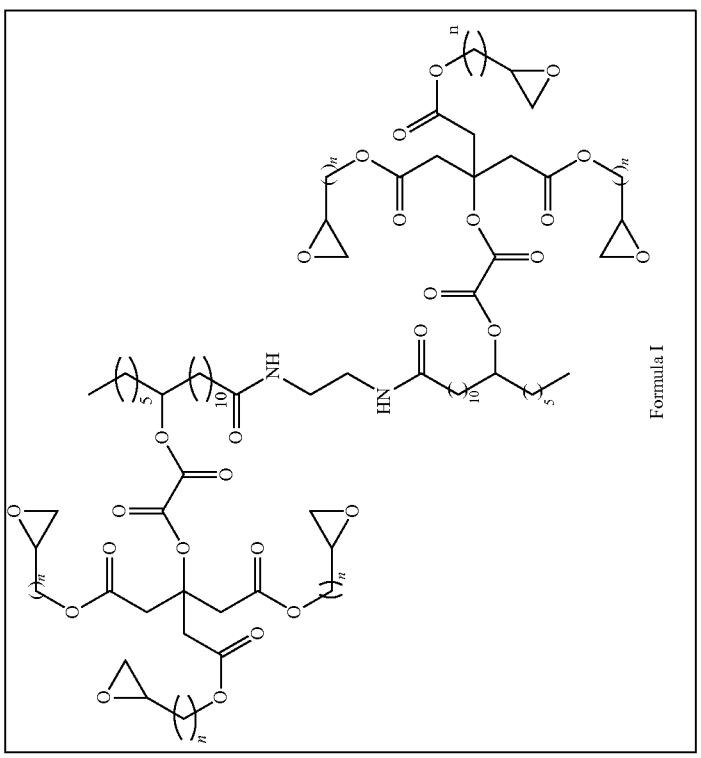
Formula I

As an exemplary embodiment, the present invention provides a synthetic method of Formula I with n being 1, in which case the structural Formula of Formula I is as shown in Formula Ia: ethylene bis-12-hydroxystearamide grafted glycidyl citrate (EBH-g-ECA), the structural Formula of Formula II is as shown in Formula IIa: ethylene bis-12-hydroxystearamide grafted citric acid olefin ester.

In another aspect, the present invention also provides during the preparation of ethylene bis-12-hydroxystearamide grafted glycidyl citrate (EBH-g-ECA) of the above Formula Ia, an intermediate product ethylene bis-12-hydroxystearic acid grafted citric acid having the structural Formula as shown in Formula IIa; and an intermediate product ethylene bis-12-hydroxystearamide grafted citric acid olefin ester having the structural Formula as shown in Formula III.

The method for preparing the above ethylene bis-12-hydroxystearamide grafted glycidyl citrate (EBH-g-ECA) comprises:

S1. uniformly mixing citric acid, oxalyl chloride, ethylene bis-12-hydroxystearamide, a catalyst with a solvent, heating to 20° C.-60° C. under the protection of an inert gas under stirring for 30-60 h, and distilling under reduced pressure to obtain ethylene bis-12-hydroxystearamide grafted citric acid (Formula III);

S2. uniformly mixing ethylene bis-12-hydroxystearamide grafted citric acid (Formula III) obtained in the step S1 with a halogenated olefin, a catalyst and a solvent, and heated to 40° C.-60° C. under the protection of an inert gas under stirring for 25 h-50 h, washing and distilling under reduced pressure to obtain ethylene bis-12-hydroxystearamide grafted citric acid olefin ester (Formula IIa).

S3. uniformly mixing ethylene bis-12-hydroxystearamide grafted citric acid olefin ester (Formula IIa) obtained in step S2 with a catalyst and a solvent, and heating same to 40° C.-60° C. under the protection of an inert gas under stirring for 20 h-50 h, washing and distilling under reduced pressure to obtain ethylene bis-12-hydroxystearamide grafted glycidyl citrate (Formula Ia).

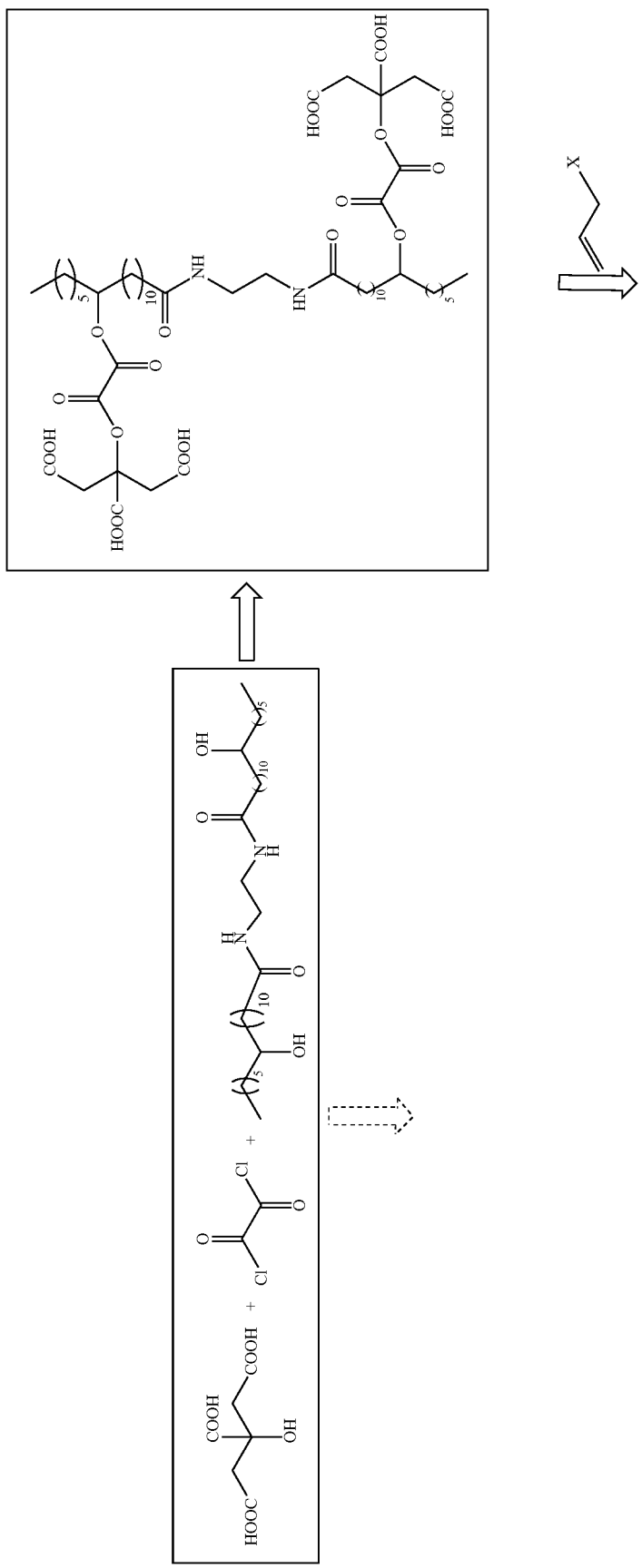

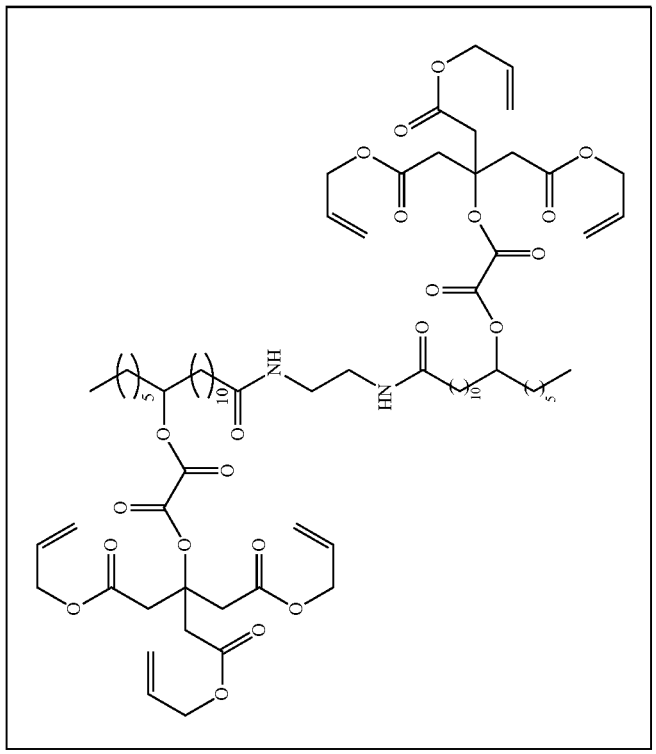
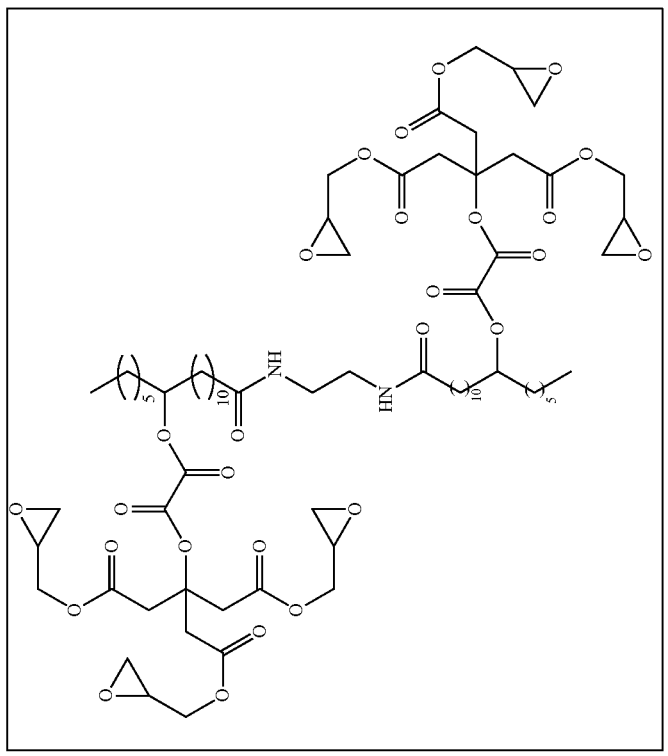

Among them, the catalyst described in S1 is selected from at least one of potassium carbonate and sodium carbonate; the solvent is selected from at least one of chloroform, toluene and tetrahydrofuran; preferably selected from chloroform; the inert gas is selected from nitrogen; among them, the molar ratio of citric acid, oxalyl chloride, ethylene bis-12-hydroxystearamide to catalyst is 2.2-2.5:2.2-2.5:1.0: 3.0-5.5; the weight ratio of citric acid to solvent is 1:8-10; the catalyst described in step S2 is at least one of potassium carbonate and sodium carbonate; the solvent is selected from at least one of dimethyl sulfoxide, N,N-dimethylformamide, toluene, and N,N-dimethylacetamide; preferably selected from N,N-dimethylformamide; the inert gas is selected from nitrogen, etc.; wherein the molar ratio of ethylene bis-12-hydroxystearamide grafted citric acid, halogenated olefin to catalyst is 1.0:7.3-9.6:2-6; the weight ratio of ethylene bis-12-hydroxystearamide grafted citric acid to solvent is 1:10-15; the halogenated olefin is selected from one of 3-bromo-1 propylene, 4-bromo-1-butene, 5-bromo-1-pentene, 6-bromo-1-hexene, 7-bromo-1-heptene, 8-bromo-1-octene, 9-bromo-1 nonene, 3-chloro-1-propene, 4-chloro-1-butene, 5-chloro-1-pentene, 6-chloro-1-hexene, 7-chloro-1-heptene, 8-chloro-1-octene, 9-chloro-1 nonene; preferably selected from 3-bromo-1-propene and 3-chloro-1-propene, more preferably selected from 3-bromo-1-propene;
the catalyst described in step S3 is selected from at least one of m-chloroperoxybenzoic acid, peroxybenzoic acid, and p-nitroperoxybenzoic acid, preferably selected from m-chloroperoxybenzoic acid; the solvent is selected from at least one of dichloromethane, trichloromethane, acetone, butanone and toluene; preferably selected from trichloromethane; the inert gas is selected from nitrogen, etc. The molar ratio of ethylene bis-12-hydroxystearamide grafted citric acid olefin ester to catalyst is 1.0:6.6-8.5; the weight ratio of ethylene bis-12-hydroxystearamide grafted citric acid olefin ester to solvent is 1:8-13.

In another aspect, the present invention provides the use of a compound shown in Formula I and an intermediate compound in the synthesis of Formula I as an internal lubricant, a release agent, an interfacial compatibilizer, a plasticizer, a chain extender, and/or a crystallization nucleating agent in the plastics field, in particular, provides EBH-g-ECA as an internal lubricant, a release agent, an interfacial compatibilizer, a plasticizer, a chain extender, and/or a crystallization nucleating agent in the plastics field.

A series of the compound shown in Formula I has both an amide group and an epoxy group, the amide group act as a nucleating agent, and the epoxy group act as a chain extender function, such that it can be used as a multifunctional auxiliary agent for polylactic acid foamed materials, and has both chain extension and crystallization nucleation effects, as well as lubrication and foam stabilizer effects.

In a preferred embodiment of the present invention, the EBH-g-ECA synthesized by the present invention is used as a multifunctional auxiliary agent functioning as both a chain extender and a crystallization nucleating agent.

The invention also provides a polylactic acid foamed material comprising ethylene bis-12-hydroxystearamide grafted glycidyl citrate (EBH-g-ECA),
preferably, the polylactic acid foamed material is made from the following components in weight percentage:

| | |
|---|---|
| polylactic acid | 90%-95%; |
| a PBAT resin | 1%-5%; |
| a cell nucleating agent | 0.1%-3%; |
| a co-blowing agent | 0.1%-3%; |
| EBH-g-ECA | 0.1%-2.0%. |

The method for preparing the EBH-g-ECA is as follows:
S1. uniformly mixing citric acid, oxalyl chloride, ethylene bis-12-hydroxystearamide, a catalyst with a solvent, heating to 20° C.-60° C. under the protection of an inert gas under stirring for 30-60 h, and distilling under reduced pressure to obtain ethylene bis-12-hydroxystearamide grafted citric acid (Formula III);
S2. uniformly mixing ethylene bis-12-hydroxystearamide grafted citric acid (Formula III) obtained in the step S1 with a halogenated olefin, a catalyst and a solvent, and heated to 40° C.-60° C. under the protection of an inert gas under stirring for 25 h-50 h, washing and distilling under reduced pressure to obtain ethylene bis-12-hydroxystearamide grafted citric acid olefin ester (Formula IIa).
S3. uniformly mixing ethylene bis-12-hydroxystearamide grafted citric acid olefin ester (Formula IIa) obtained in step S2 with a catalyst and a solvent, and heating same to 40° C.-60° C. under the protection of an inert gas under stirring for 20 h-50 h, washing and distilling under reduced pressure to obtain ethylene bis-12-hydroxystearamide grafted glycidyl citrate (Formula Ia).

Among them, the catalyst described in S1 is selected from at least one of potassium carbonate or sodium carbonate; the solvent is selected from at least one of chloroform, toluene and tetrahydrofuran; preferably selected from chloroform; the inert gas is nitrogen; the molar ratio of citric acid, oxalyl chloride, ethylene bis-12-hydroxystearamide to catalyst is 2.2-2.5:2.2-2.5:1.0:3.0-5.5; the weight ratio of citric acid to solvent is 1:8-10.

The catalyst described in step S2 is at least one of potassium carbonate and sodium carbonate; the solvent is selected from at least one of dimethyl sulfoxide, N,N-dimethylformamide, toluene, and N,N-dimethylacetamide; preferably selected from N,N-dimethylformamide; the inert gas is selected from nitrogen, etc.; the molar ratio of ethylene bis-12-hydroxystearamide grafted citric acid, halogenated olefin to catalyst is 1.0:7.3-9.6:2-6; the weight ratio of ethylene bis-12-hydroxystearamide grafted citric acid to solvent is 1:10-15; the halogenated olefin is selected from one of 3-bromo-1 propylene, 4-bromo-1-butene, 5-bromo-1-pentene, 6-bromo-1-hexene, 7-bromo-1-heptene, 8-bromo-1-octene, 9-bromo-1 nonene, 3-chloro-1-propene, 4-chloro-1-butene, 5-chloro-1-pentene, 6-chloro-1-hexene, 7-chloro-1-heptene, 8-chloro-1-octene, 9-chloro-1 nonene; preferably selected from 3-bromo-1-propene and 3-chloro-1-propene, more preferably selected from 3-bromo-1-propene.

The catalyst described in step S3 is selected from at least one of m-chloroperoxybenzoic acid, peroxybenzoic acid, and p-nitroperoxybenzoic acid, preferably selected from m-chloroperoxybenzoic acid; the solvent is selected from at least one of dichloromethane, trichloromethane, acetone, butanone and toluene, preferably selected from trichloromethane; the inert gas is nitrogen. The molar ratio of ethylene bis-12-hydroxystearamide grafted citric acid olefin ester to catalyst is 1.0:6.6-8.5; the weight ratio of ethylene bis-12-hydroxystearamide grafted citric acid olefin ester to solvent is 1:8-13.

The polylactic acid is one or a mixture of two or more of L-type polylactic acid, D-type polylactic acid and LD-mixed type polylactic acid, and the polylactic acid has a weight average molecular weight of 100,000-300,000, and a molecular weight distribution Mw/Mn of 1.3-1.8.

The PBAT resin is a copolymer of butylene adipate and butylene terephthalate, and the PBAT resin has a biological weight average molecular weight of 50,000-80,000 and a molecular weight distribution Mw/Mn of 1.2-1.6.

The cell nucleating agent is one or two of talcum powder, nano mica, nano organic montmorillonite, etc.

The co-blowing agent is selected from one or two or more of a citric acid fatty acid glyceride, a polyoxyethylene sorbitan fatty acid ester, a sorbitan fatty acid, a castor oil polyoxyethylene ether, etc.

In addition to the above-mentioned components, the polylactic acid foamed material according to the present invention may comprises other components, which may be added to the composition of the present invention as long as it does not affect the properties of the polylactic acid foamed material according to the present invention, such as colorants, antioxidants, toughening agents, lubricants, fillers, brighteners, etc.

In the existing research, the chain extender and crystallization nucleating agent have been used to improve the melt strength and heat resistance of polylactic acid; however, the effect of improvement is very limited, or although the problem of melt strength or heat resistance is solved, new problems have arisen, such as a large cell size, uneven cells, low mechanical properties of the foamed material, etc.

The prior patent CN 105219044 A, which belongs to the applicant of the present technical solution, discloses a heat-resistant polylactic acid foamed material which uses a separate chain extender (ADR4368C/CS, BASF AG) and a crystallization nucleating agent (ethylene bis-12-hydroxystearamide, EBH) for improving the heat resistance of polylactic acid foamed materials. Although the heat resistance of the foamed material is improved to some extent, it is unsatisfactory that the foamed material has a rough appearance, insufficient aesthetics, and low mechanical properties of the product.

The inventors have also simultaneously added ethylene bis-12-hydroxystearamide (EBH) and glycidyl citrate (ECA) as foaming auxiliaries for a polylactic acid foamed material to a polylactic acid foamed material (see Comparative Example 2), leading to a greater material density of 0.26 $g/cm^3$, which is about twice the density of the foamed material prepared by the present technical solution (0.11-0.16 $g/cm^3$) and thus is not conducive to reducing the application cost of the polylactic acid.

Therefore, during the actual production and application of the foaming auxiliaries, it is difficult to have an auxiliary agent or a combination of several auxiliary agent capable of simultaneously improving the melt strength, heat resistance, and ensuring a small cell size, a large cell density, uniform cells of the foamed material, and ensuring a small density of the foamed material. In order to solve the problem that the auxiliary agent of the polylactic acid foamed material in the prior art has at least one unsatisfactory parameter and it is difficult to realize the industrial production of the polylactic acid foamed material, after several attempts, the inventors finally synthesized a multifunctional auxiliary agent, ethylene bis-12-hydroxystearamide grafted glycidyl citrate (EBH-g-ECA).

The EBH-g-ECA synthesized in the present invention has both chain extension (increasing melt strength) and crystallization nucleation (increasing heat resistance) effects in the polylactic acid foamed material. At the same time, the prepared EBH-g-ECA relates to the use of citric acid with a wide source and a low price as a raw material, and the prepared EBH-g-ECA has a high epoxy value, which is economical, environmentally friendly and has a low price. The price of the market's existing multi-functional chain extenders such as BASF ADR-4368CS is as high as 380 yuan/KG. Most importantly, the EBH-g-ECA according to the present invention performs more excellent than the existing chain extender and crystallization nucleating agent compounding systems, mainly because the multifunctional auxiliary agent connects a plurality of polylactic acid molecular chains together, thereby promoting the amide functional group to exhibit more excellent crystal nucleation (the amide functional group is at the linkage of a plurality of polylactic acid molecular chains). The increase in crystallinity enhances the heat resistance of the polylactic acid foamed material. The polylactic acid foamed material prepared in the invention has a heat distortion temperature of more than 115° C. More beneficially, in the present invention, EBH-g-ECA is compounded with other auxiliary agents such as a co-blowing agent, a cell nucleating agent, etc., while ensuring heat resistance and improving the strength of the melt, the cells are even and fine, and the appearance of the product is uniform, which ensures the excellent mechanical properties of the foamed material, and the material density of the foamed material is low, which reduces the application cost of the polylactic acid.

The invention also provides a preparation method of a fully biodegradable heat-resistant polylactic acid foamed material, which has a simple process, is easy to control, has a strong operability, a continuous production, and is easy to implement industrially. The specific process is as follows:

(1). drying the polylactic acid with a high-speed mixer at 100° C.-110° C. for 20-40 min, then adding other auxiliary agents and mixing uniformly; then, adding the mixed materials to a twin-screw extruder, melt-blending, stranding, air-cooling, and pelletizing to obtain heat-resistant polylactic acid particles, which are packing under vacuum. In such a case, the length to diameter ratio of screw in the twin-screw extruder was 36:1-48:1; the melt blending temperature was from 180° C. to 200° C.

(2). adding the heat-resistant polylactic acid foamed material particles obtained in the step S4 to a twin-screw material forming machine, and melt-blending and extruding by using carbon dioxide, pentane, butane or Freon as a blowing agent, and melt blending and extrusion to finally obtain a heat-resistant polylactic acid foamed material.

The heat-resistant polylactic acid foamed material has a high melt strength, a wide processing window, a fast crystallization rate, a good heat resistance, and maintains its own full biodegradation advantage. In addition, the heat-resistant polylactic acid foamed material prepared by using twin-screw continuous extrusion, and using carbon dioxide, nitrogen, pentane, butane or Freon as a physical blowing agent has an advantage of a foaming ratio of 10-20, a uniform cell size, and a high closed cell ratio.

The physical blowing agent used in the present invention is one or a combination of more of carbon dioxide, nitrogen, pentane, butane or Freon; preferably, one or a combination of carbon dioxide and nitrogen; it is particularly preferred to use a mixture of supercritical carbon dioxide and nitrogen (the volume ratio of carbon dioxide to nitrogen is 20%:80%) as the main blowing agent. Carbon dioxide and nitrogen are non-toxic, harmless, non-polluting and non-combustible, and carbon dioxide has excellent regulation and control of swelling and osmosis of the polymers, making the cell size finer; and nitrogen helps the cell to grow, ensuring a lower density of the polylactic acid foamed material.

Another outstanding advantage of the present invention is that continuous twin-screw foaming can be achieved. The preparation of polylactic acid foamed material by twin-screw continuous extrusion is of a great significance for realizing the industrial application of polylactic acid foamed material. In the prior art, the production of polylactic acid continuous foamed materials is immature, and many scholars have studied polylactic acid foaming, such as Yang Zhiyun et al. (2014, Vol. 33, Supplement 1, Chemical Progress), who studied the influencing factors for the cell structure of the continuous extrusion foaming polylactic acid with single-screw continuous foaming. Compared with a single screw, a twin screw has a higher shear rotation number, allows easier uniform mixing of the blowing agent, helps to increase the number of cells, allows a more regular cell structure, a more uniform cell shape, and a higher production efficiency. The twin-screw continuous extrusion foaming has higher requirements on the melt strength of the polymer material, and the low melt strength polylactic acid has a lower performance under high shear state. Therefore, the twin-screw continuous foaming is difficult to apply to the production of polylactic acid foamed materials. Ma Yuwu et al. (Ma Yuwu, Xin Chunling, He Yadong, et al. Effect of supercritical $CO_2$ on extrusion foaming of polylactic acid [J]. China Plastics, 2012, 26(12): 72-75) prepared polylactic acid foamed material with twin-screw extrusion foaming, however, the foamed material as prepared has a cell size of 285 μm, and its physical and mechanical properties are much lower than those of the polylactic acid foamed material prepared by the present invention.

Compared with the prior art, the present invention has the following advantages:
(1) The multifunctional auxiliary agent prepared in the invention is a series of polymers shown in Formula I, including ethylene bis-12-hydroxystearamide grafted glycidyl citrate, and which have both chain extension and crystallization nucleation effects. On the one hand, this multifunctional auxiliary agent contains a plurality of epoxy functional groups, which can greatly increase the molecular weight and molecular chain length of the polylactic acid by branching, thereby improving the melt strength of the polylactic acid and broadening the processing window of the polylactic acid, and finally solving the limitation of the low melt strength and the narrow processing window of the polylactic acid on the foaming of polylactic acid materials; On the other hand, this multifunctional auxiliary agent contains an amide functional group and has excellent crystallization nucleation effect on polylactic acid, which can greatly improve the crystallization nucleation rate and crystallinity of the polylactic acid, and ensure that the polylactic acid crystal size is small and uniform, thereby solving the problem of poor heat resistance of the polylactic acid. The multifunctional auxiliary agent according to the present invention performs more excellent than the existing chain extender and crystallization nucleating agent compounding systems, mainly because the multifunctional auxiliary agent connects a plurality of polylactic acid molecular chains together, thereby promoting the amide functional group to exhibit more excellent crystal nucleation (the amide functional group is at the linkage of a plurality of polylactic acid molecular chains).
(2) The polylactic acid foamed material prepared by the prior art has defects of a low foaming rate, a uneven cell size and a high opening rate, which is mainly caused by uncontrolled growth of polylactic acid cells. Through the screening of a large number of co-blowing agents, an auxiliary agent which has a stabilizing effect on the foaming of polylactic acid is finally obtained, thereby realizing the controllability of the growth of polylactic acid cells, and finally obtaining a polylactic acid foamed material having the advantages of a uniform cell size and a high closed cell ratio. This is mainly because the co-blowing agent selected in the invention can effectively improve the affinity of the polylactic acid and the foaming gas interface, and realize the stable growth of the polylactic acid cells, thereby overcoming the problem of an uneven size and a high opening ratio of the polylactic acid cells.
(3) The heat-resistant polylactic acid foamed material prepared in the present invention can realize twin-screw continuous foaming by using foaming technology such as supercritical carbon dioxide, nitrogen, pentane, butane or Freon, and the prepared plastic product has a heat-resistant temperature of 115° C. or higher, the foaming ratio can be controlled to 10-20, the cell size distribution is uniform, and the closed cell ratio is high, which are of a great significance for realizing large-scale replacement of foamed materials such as PS.

DETAILED DESCRIPTION OF THE EMBODIMENTS

The technical solutions of the present invention are further illustrated by the following specific examples, which are not intended to limit the scope of the present invention. Some non-essential modifications and adaptations made by others in accordance with the teachings of the present invention are still within the scope of the present invention.

The following examples illustrate only embodiments of the invention with compounds wherein n is 1 in Formula I, a series of compound shown in Formula I has multiple amide groups and epoxy groups at the same time, the amide group acts as a nucleating agent, and the epoxy group acts as a chain extender function, such that the compound can be used as a multifunctional auxiliary agent for polylactic acid foamed materials, and has both chain extension and crystallization nucleation effects, as well as lubrication and a foam stabilizer effects.

EXAMPLE 1

Figure 1:
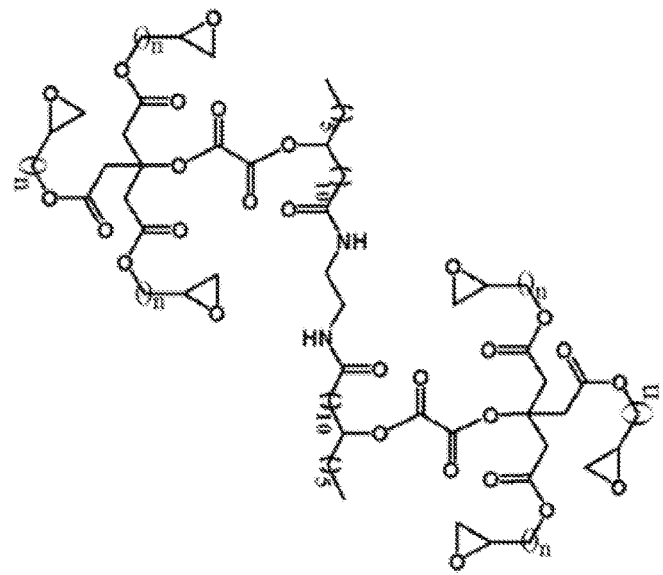
FIG. 1 shows the structural Formula of the Formula I.
Figure 2:
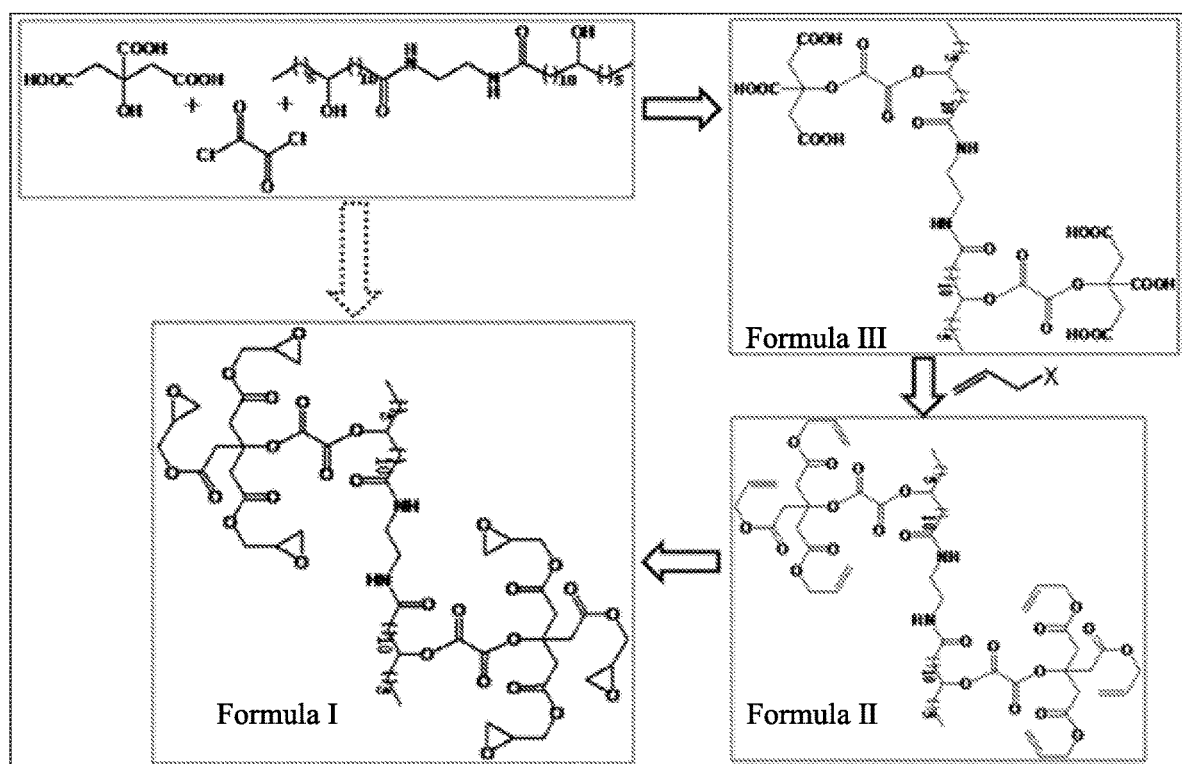
FIG. 2 shows the synthetic route of the Formula I.
Figure 3:
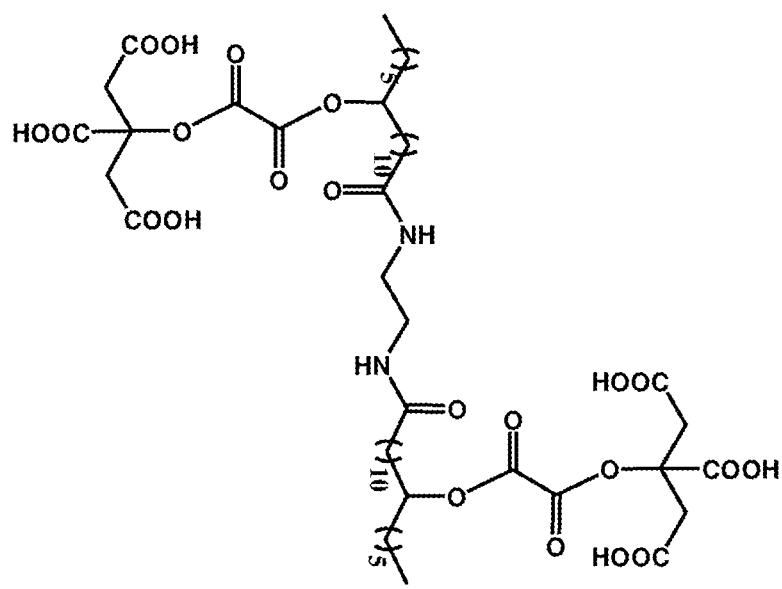
FIG. 3 shows the structural Formula of the Formula III.
Figure 4:
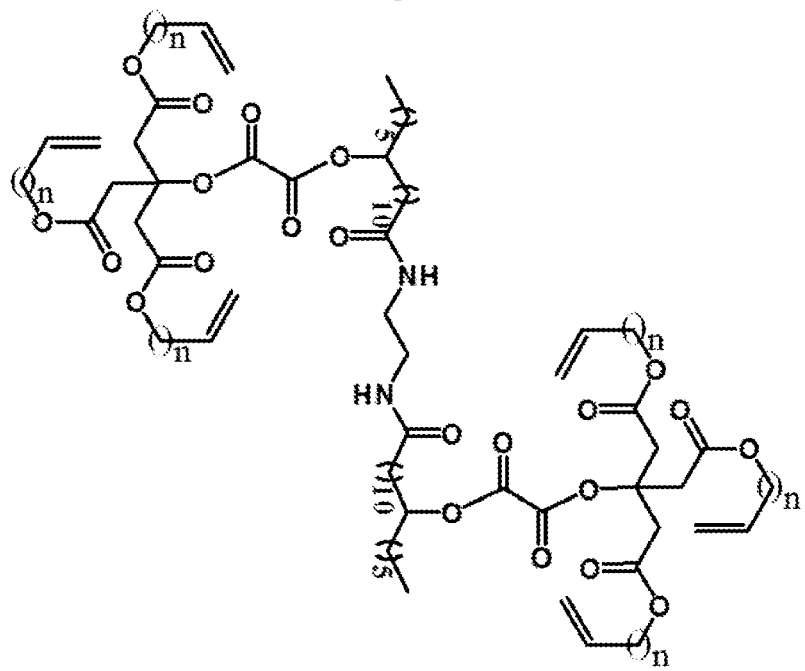
FIG. 4 shows the structural Formula of the Formula II.
Figure 5:
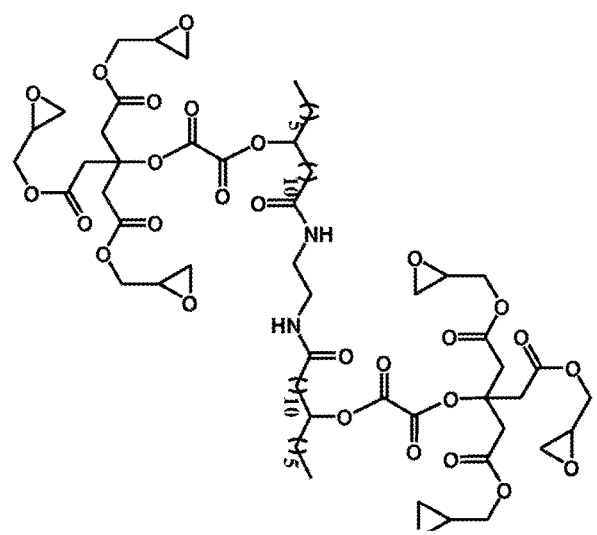
FIG. 5 shows the structural Formula of the Formula Ia.
Figure 6:
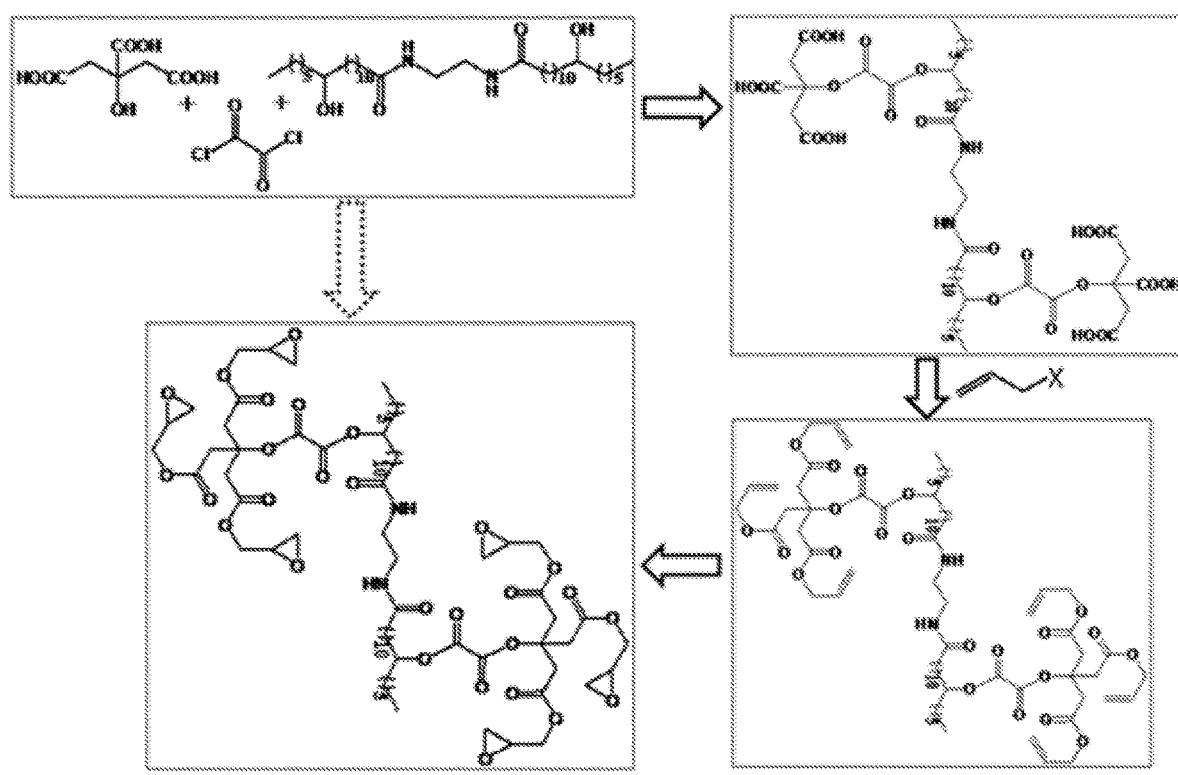
FIG. 6 shows the synthetic route of Formula Ia.
Figure 7:
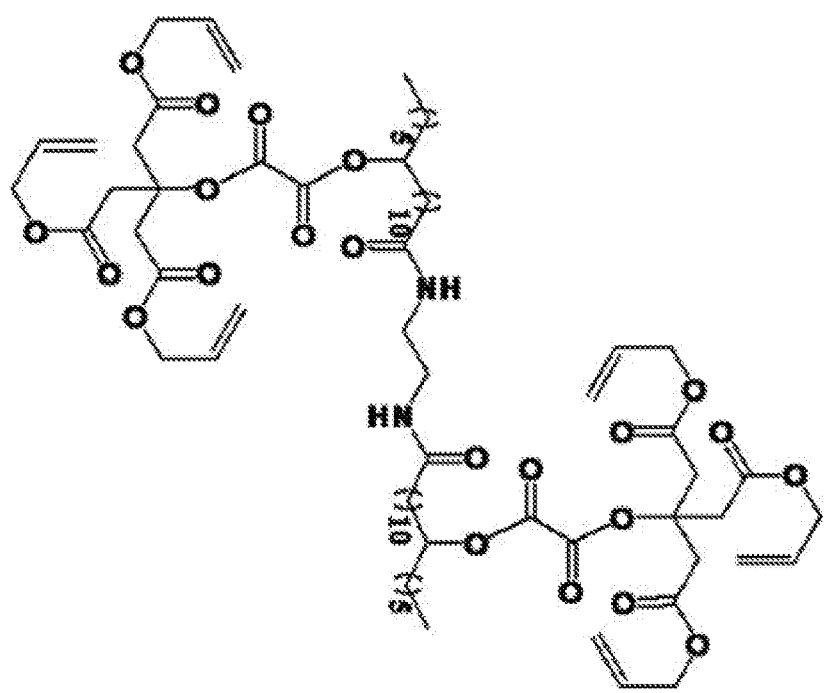
FIG. 7 shows the structural Formula of the Formula IIa.
Figure 8:
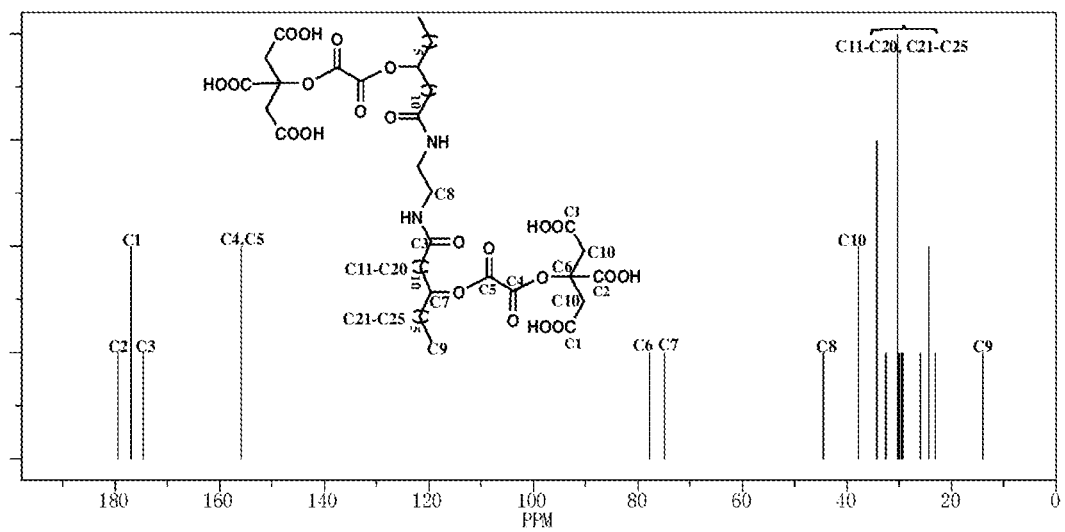
FIG. 8 is a graph showing the carbon nuclear magnetic spectrum of the ethylene bis-12-hydroxystearamide grafted citric acid (Formula III) prepared in the present invention.

Method for Preparing Ethylene Bis-12-Hydroxystearamide Grafted Glycidyl Citrate (1) 50 g (0.26 mol) of citric acid, 33 g (0.26 mol) of oxalyl chloride, 68.6 g (0.11 mol) of ethylenebis-12-hydroxystearamide, 106 g (1.0 mol) of sodium carbonate, and 400 g of chloroform were added in a 1000 ml four-necked flask, mixed uniformly, heated to 60° C. under the protection of an inert gas under stirring, reacted for 45 h, and distilled under reduced pressure to obtain 66.8 g of ethylene bis-12-hydroxystearamide grafted citric acid. The carbon nuclear magnetic spectrum of the prepared ethylene bis-12-hydroxystearamide grafted citric acid is shown in FIG. 8, wherein C1=177 ppm and C2=180 ppm are characteristic peaks of carbon on the carboxyl group in citric acid.

Figure 9:
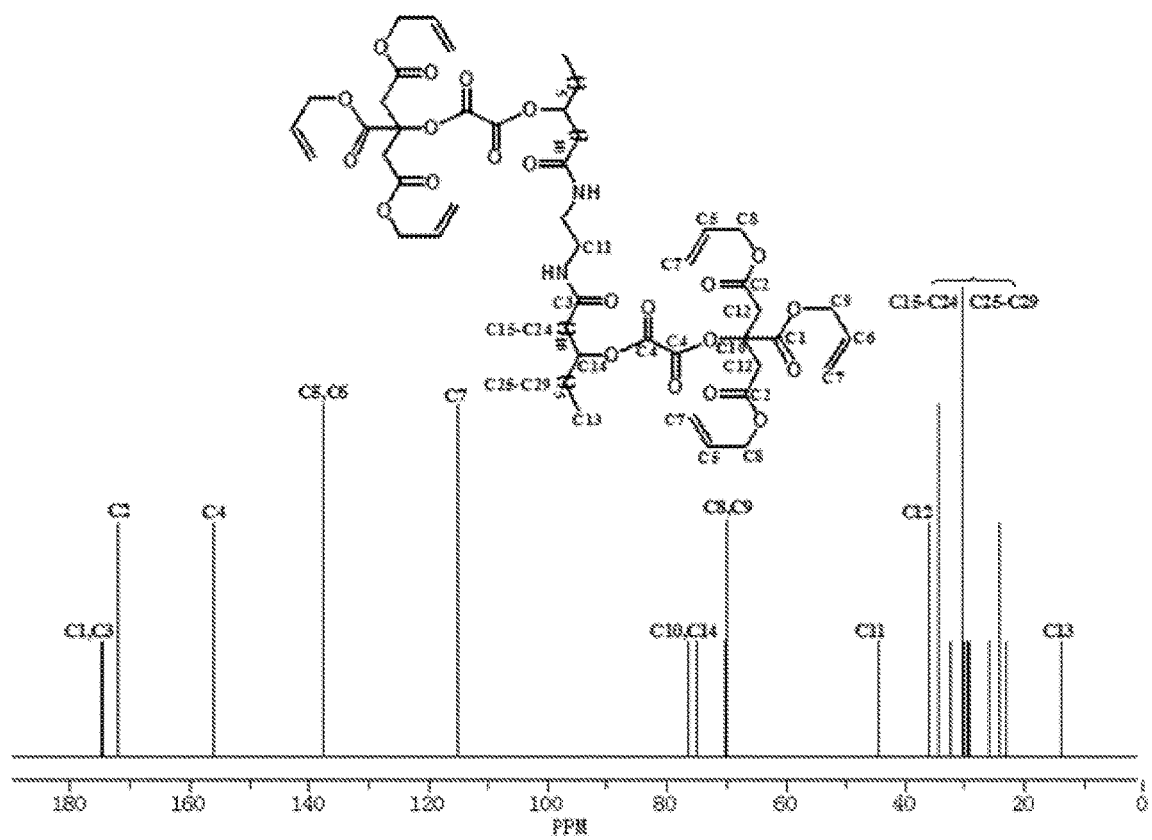
FIG. 9 is a graph showing the carbon nuclear magnetic spectrum of the ethylene bis-12-hydroxystearamide grafted citric acid olefin ester (Formula IIa) prepared in the present invention.

(2) 55.8 g (0.05 mol) of ethylene bis-12-hydroxystearamide grafted citric acid obtained in the step (1), 48.4 g (0.4 mol) of bromopropene, 53 g (0.5 mol) of sodium carbonate, and 600 g of N,N-dimethylformamide were added in a three-necked flask, heated to 60° C. under the protection of an inert gas under stirring, reacted for 35 h, washed and distilled under reduced pressure to obtain 51.3 g of ethylene bis-12-hydroxystearamide grafted allyl citrate. The carbon nuclear magnetic spectrum of the prepared ethylene bis-12-hydroxystearamide grafted allyl citrate is shown in FIG. 9, wherein C5/C6=138 ppm and C7=116 ppm are characteristic peaks of carbon in the carbon-carbon double bond on the allyl group.

Figure 10:
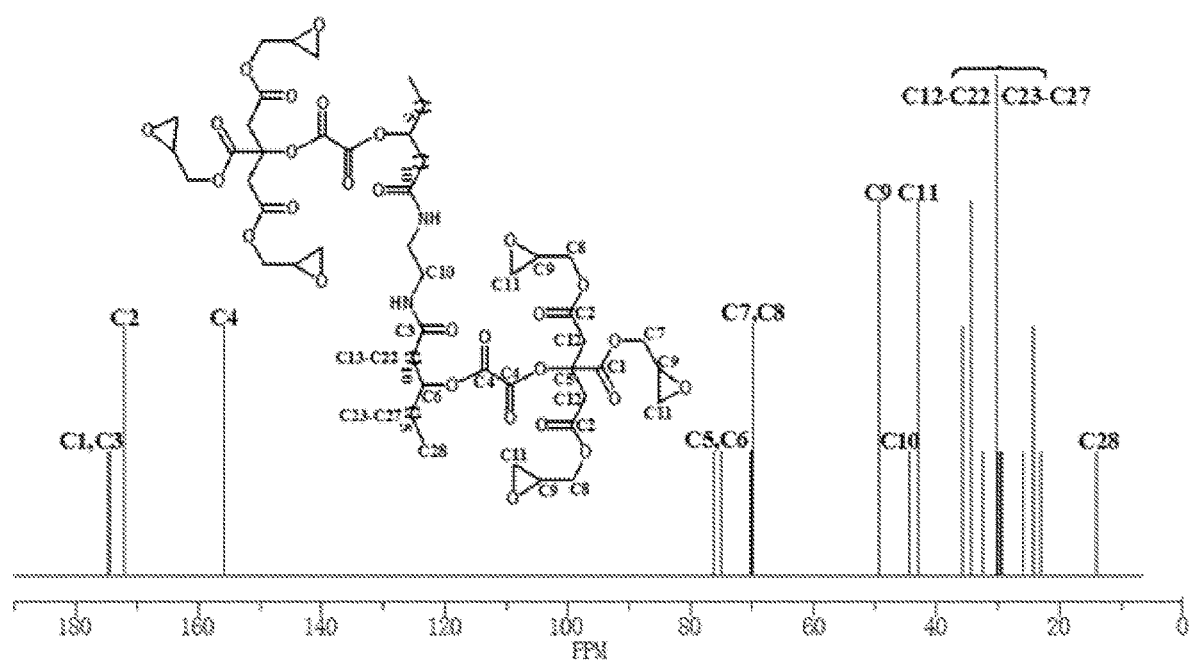
FIG. 10 is a graph showing the carbon nuclear magnetic spectrum of the ethylene bis-12-hydroxystearamide grafted glycidyl citrate (Formula Ia) prepared in the present invention.

(3) 67.8 g (0.05 mol) of ethylene bis-12-hydroxystearamide grafted allyl citrate obtained in the step (2), 60.5 g (0.35 mol) of m-chloroperoxybenzoic acid, and 700 g of trichloromethane were added in a three-necked flask, heated to 50° C. under the protection of an inert gas under stirring, reacted for 30 h, washed and distilled under reduced pressure to obtain 23.5 g of ethylene bis-12-hydroxystearamide grafted glycidyl citrate. The carbon nuclear magnetic spectrum of the prepared ethylene bis-12-hydroxystearamide grafted glycidyl citrate is shown in FIG. 10, wherein C11=45 ppm and C9=49 ppm are characteristic peaks of carbon on the epoxy group.

EXAMPLE 2

Method for Preparing Ethylene Bis-12-Hydroxystearamide Grafted Glycidyl Citrate (1) 50 g (0.26 mol) of citric acid, 33 g (0.26 mol) of oxalyl chloride, 68.6 (0.11 mol) of ethylenebis-12-hydroxystearamide, 138 g (1.0 mol) of potassium carbonate, and 400 g of chloroform were added in a 1000 ml four-necked flask, mixed uniformly, heated to 60° C. under the protection of an inert gas under stirring, reacted for 45 h, and distilled under reduced pressure to obtain 62.5 g of ethylene bis-12-hydroxystearamide grafted citric acid. The carbon nuclear magnetic spectrum of the prepared ethylene bis-12-hydroxystearamide grafted citric acid is similar to FIG. 8.

(2) 55.8 g (0.05 mol) of ethylene bis-12-hydroxystearamide grafted citric acid obtained in the step (1), 48.4 g (0.4 mol) of bromopropene, 69 g (0.5 mol) of potassium carbonate, and 600 g of N,N-dimethylformamide were added in a three-necked flask, heated to 60° C. under the protection of an inert gas under stirring, reacted for 35 h, washed and distilled under reduced pressure to obtain 53 g of ethylene bis-12-hydroxystearamide grafted allyl citrate. The carbon nuclear magnetic spectrum of the prepared ethylene bis-12-hydroxystearamide grafted allyl citrate is similar to FIG. 9.

(3) 67.8 g (0.05 mol) of ethylene bis-12-hydroxystearamide grafted allyl citrate obtained in the step (2), 60.5 g (0.35 mol) of m-chloroperoxybenzoic acid, and 700 g of trichloromethane were added in a three-necked flask, heated to 50° C. under the protection of an inert gas under stirring, reacted for 30 h, washed and distilled under reduced pressure to obtain 25.4 g of ethylene bis-12-hydroxystearamide grafted glycidyl citrate. The carbon nuclear magnetic spectrum of the prepared ethylene bis-12-hydroxystearamide grafted glycidyl citrate is similar to FIG. 10.

EXAMPLE 3

Method for Preparing Ethylene Bis-12-Hydroxystearamide Grafted Glycidyl Citrate (1) 50 g (0.26 mol) of citric acid, 33 g (0.26 mol) of oxalyl chloride, 68.6 g (0.11 mol) of ethylenebis-12-hydroxystearamide, 106 g (1.0 mol) of sodium carbonate, and 400 g of chloroform were added in a 1000 ml four-necked flask, mixed uniformly, heated to 60° C. under the protection of an inert gas under stirring, reacted for 45 h, and distilled under reduced pressure to obtain 64.6 g of ethylene bis-12-hydroxystearamide grafted citric acid. The carbon nuclear magnetic spectrum of the prepared ethylene bis-12-hydroxystearamide grafted citric acid is similar to FIG. 8.

(2) 55.8 g (0.05 mol) of ethylene bis-12-hydroxystearamide grafted citric acid obtained in the step (1), 48.4 g (0.4 mol) of bromopropene, 53 g (0.5 mol) of sodium carbonate, and 600 g of N,N-dimethylformamide were added in a three-necked flask, heated to 60° C. under the protection of an inert gas under stirring, reacted for 35 h, washed and distilled under reduced pressure to obtain 52.6 g of ethylene bis-12-hydroxystearamide grafted allyl citrate. The carbon nuclear magnetic spectrum of the prepared ethylene bis-12-hydroxystearamide grafted allyl citrate is similar to FIG. 9.

(3) 67.8 g (0.05 mol) of ethylene bis-12-hydroxystearamide grafted allyl citrate obtained in the step (2), 55.2 g (0.4 mol) of peroxybenzoic acid, and 700 g of trichloromethane were added in a three-necked flask, heated to 50° C. under the protection of an inert gas under stirring, reacted for 30 h, washed and distilled under reduced pressure to obtain 21.3 g of ethylene bis-12-hydroxystearamide grafted glycidyl citrate. The carbon nuclear magnetic spectrum of the prepared ethylene bis-12-hydroxystearamide grafted glycidyl citrate is similar to FIG. 10.

EXAMPLE 4

Method for Preparing Ethylene Bis-12-Hydroxystearamide Grafted Glycidyl Citrate (1) 50 g (0.26 mol) of citric acid, 33 g (0.26 mol) of oxalyl chloride, 68.6 (0.11 mol) of ethylenebis-12-hydroxystearamide, 138 g (1.0 mol) of potassium carbonate, and 400 g of chloroform were added in a 1000 ml four-necked flask, mixed uniformly, heated to 60° C. under the protection of an inert gas under stirring, reacted for 45 h, and distilled under reduced pressure to obtain 62.5 g of ethylene bis-12-hydroxystearamide grafted citric acid. The carbon nuclear magnetic spectrum of the prepared ethylene bis-12-hydroxystearamide grafted citric acid is similar to FIG. 8.

(2) 55.8 g (0.05 mol) of ethylene bis-12-hydroxystearamide grafted citric acid obtained in the step (1), 30.6 g (0.4 mol) of chloropropene, 69 g (0.5 mol) of potassium carbonate, and 600 g of N,N-dimethylformamide were added in a three-necked flask, heated to 60° C. under the protection of an inert gas under stirring, reacted for 35 h, washed and distilled under reduced pressure to obtain 51.3 g of ethylene bis-12-hydroxystearamide grafted allyl citrate. The carbon nuclear magnetic spectrum of the prepared ethylene bis-12-hydroxystearamide grafted allyl citrate is similar to FIG. 9.

(3) 67.8 g (0.05 mol) of ethylene bis-12-hydroxystearamide grafted allyl citrate obtained in the step (2), 60.5 g (0.35 mol) of m-chloroperoxybenzoic acid, and 700 g of trichloromethane were added in a three-necked flask, heated to 50° C. under the protection of an inert gas under stirring, reacted for 30 h, washed and distilled under reduced pressure to obtain 25.1 g of ethylene bis-12-hydroxystearamide grafted glycidyl citrate. The carbon nuclear magnetic spectrum of the prepared ethylene bis-12-hydroxystearamide grafted glycidyl citrate is similar to FIG. 10.

EXAMPLE 5

Preparation of Heat-Resistant Polylactic Acid Foamed Material

The following raw materials were weighed:
92 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 0.5 Kg of a co-blowing agent (citric acid fatty acid glyceride, Shanghai Mengji Industrial Co., Ltd.), and 0.5 Kg of EBH-g-ECA (ethylene bis-12-hydroxystearamide grafted glycidyl citrate, homemade).

Method for Preparing a Heat-Resistant Polylactic Acid Foamed Material:
(1) the polylactic acid was dried with a high-speed mixer at 105° C. for 30 min, then other auxiliary agents were added and mixed uniformly; then, the mixed materials were added to a twin-screw extruder, melt-blended, stranded, air-cooled, and pelletized to obtain modified polylactic acid particles, which were packed under vacuum. In such a case, the length to diameter ratio of screw in the twin-screw extruder was 36:1-48:1; the melt blending temperature was from 180° C. to 200° C.
(2) The heat-resistant polylactic acid foamed material particles obtained in the step (1) were added into a twin-screw material forming machine, and melt-blended and extruded by using a mixture of carbon dioxide and nitrogen (a volume ratio of carbon dioxide to nitrogen was 20%:80%) as a blowing agent to finally obtain a heat-resistant polylactic acid foamed material.

EXAMPLE 6

Preparation of Heat-Resistant Polylactic Acid Foamed Material

The following raw materials were weighed:
91 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 1 Kg of a co-blowing agent (citric acid fatty acid glyceride, Shanghai Mengji Industrial Co., Ltd.), and 1 Kg of EBH-g-ECA (ethylene bis-12-hydroxystearamide grafted glycidyl citrate, homemade).
The preparation method was as described in Example 5.

EXAMPLE 7

Preparation of Heat-Resistant Polylactic Acid Foamed Material

The following raw materials were weighed:
90.5 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 1 Kg of a co-blowing agent (citric acid fatty acid glyceride, Shanghai Mengji Industrial Co., Ltd.), and 1.5 Kg of EBH-g-ECA (ethylene bis-12-hydroxystearamide grafted glycidyl citrate, homemade).
The preparation method was as described in Example 5.

EXAMPLE 8

Preparation of Heat-Resistant Polylactic Acid Foamed Material

The following raw materials were weighed:
90 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 1 Kg of a co-blowing agent (citric acid fatty acid glyceride, Shanghai Mengji Industrial Co., Ltd.), and 2 Kg of EBH-g-ECA (ethylene bis-12-hydroxystearamide grafted glycidyl citrate, homemade).
The preparation method was as described in Example 5.

EXAMPLE 9

Preparation of Heat-Resistant Polylactic Acid Foamed Material

The following raw materials were weighed:
91.5 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 0.5 Kg of a co-blowing agent (citric acid fatty acid glyceride, Shanghai Mengji Industrial Co., Ltd.), and 1.5 Kg of EBH-g-ECA (ethylene bis-12-hydroxystearamide grafted glycidyl citrate, homemade).
The preparation method was as described in Example 5.

EXAMPLE 10

Preparation of Heat-Resistant Polylactic Acid Foamed Material

The following raw materials were weighed:
90 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 1.5 Kg of a co-blowing agent (citric acid fatty acid glyceride, Shanghai Mengji Industrial Co., Ltd.), and 1.5 Kg of EBH-g-ECA (ethylene bis-12-hydroxystearamide grafted glycidyl citrate, homemade).
The preparation method was as described in Example 5.

EXAMPLE 11

Preparation of Heat-Resistant Polylactic Acid Foamed Material

The following raw materials were weighed:
90.5 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (talc powder, 5000 mesh, Dandong Tianci Flame Retardant Material Technology Co., Ltd.), 1.0 Kg of a co-blowing agent (citric acid fatty acid glyceride, Shanghai Mengji Industrial Co., Ltd.), and 1.5 Kg of EBH-g-ECA (ethylene bis-12-hydroxystearamide grafted glycidyl citrate, homemade).
The preparation method was as described in Example 5.

EXAMPLE 12

Preparation of a Heat-Resistant Polylactic Acid Foamed Material

The following raw materials were weighed:
90.5 Kg of polylactic acid (USA Natureworks 4032D), 5 Kg of a PBAT resin (Biocosafe2003, Yifan Xinfu Pharmaceutical Co., Ltd.), 2 Kg of a cell nucleating agent (nano organic montmorillonite DK-2, Zhejiang Fenghong Clay Chemical Co., Ltd.), 1.0 Kg of a co-blowing agent (polyoxyethylene sorbitan fatty acid ester T-80, Shanghai Yanwang Industrial Co., Ltd.), and 1.5 Kg of EBH-g-ECA (ethylene bis-12-hydroxystearamide grafted glycidyl citrate, homemade).

The preparation method was as described in Example 5.

COMPARATIVE EXAMPLE 1

Preparation of Polylactic Acid Material (A Chain Extender and a Crystallization Nucleating Agent were Used in Compound)

The following raw materials were weighed:
88 Kg of Polylactic acid (4032D, Natureworks, USA), 5 Kg of a PBAT resin (Biocosafe 2003, Yifan Xinfu Pharmaceutical Co., Ltd.), 1 Kg of a chain extender (ADR4368C/CS, BASF AG), 1 kg of a crystallization nucleating agent (Ethylene bis-12-hydroxystearamide EBH, Suzhou Liansheng Chemical Co., Ltd.); 2 Kg of a cell nucleating agent (nano organic montmorillonite DK-2, Zhejiang Fenghong Clay Chemical Co., Ltd.), and 1 Kg of a co-blowing agent (citric acid fatty acid glyceride, Shanghai Mengji Industrial Co., Ltd.).

The preparation method was as described in Example 5.

COMPARATIVE EXAMPLE 2

Preparation of Polylactic Acid Material (a Chain Extender, a Crystallization Nucleating Agent and Glycidyl Citrate were Used in Compound)

The following raw materials were weighed:
88 Kg of Polylactic acid (4032D, Natureworks, USA), 5 Kg of a PBAT resin (Biocosafe 2003, Yifan Xinfu Pharmaceutical Co., Ltd.), 1 Kg of a chain extender (ADR4368C/CS, BASF AG), 1 kg of a crystallization nucleating agent (Ethylene bis-12-hydroxystearamide EBH, Suzhou Liansheng Chemical Co., Ltd.); 1 kg of Triglycidyl citrate (homemade), 2 kg of a cell nucleating agent (nano organic montmorillonite DK-2, Zhejiang Fenghong Clay Chemical Co., Ltd.), and 1 Kg of a co-blowing agent (citric acid fatty acid glyceride, Shanghai Mengji Industrial Co., Ltd.).

The preparation method was as described in Example 5.

COMPARATIVE EXAMPLE 3

Preparation of Polylactic Acid Material (No Co-Blowing Agent)

The following raw materials were weighed:
91.5 Kg of polylactic acid (USA Natureworks 4032D), 5 Kg of a PBAT resin (Biocosafe2003, Yifan Xinfu Pharmaceutical Co., Ltd.), 2 Kg of a foaming nucleating agent (nano organic montmorillonite DK-2, Zhejiang Fenghong Clay Chemical Co., Ltd.), and 1.5 Kg of EBH-g-ECA (ethylene bis-12-hydroxystearamide grafted glycidyl citrate, homemade).

The preparation method was as described in Example 5.

COMPARATIVE EXAMPLE 4

Preparation of Polylactic Acid Material (No Multi-Functional Auxiliary Agent)

The following raw materials were weighed:
92 Kg of polylactic acid (USA Natureworks 4032D), 5 Kg of a PBAT resin (Biocosafe2003, Yifan Xinfu Pharmaceutical Co., Ltd.), 2 Kg of a foaming nucleating agent (nano organic montmorillonite DK-2, Zhejiang Fenghong Clay Chemical Co., Ltd.), and 1 Kg of a co-blowing agent (citric acid fatty acid glyceride, Shanghai Mengji Industrial Co., Ltd.).

The preparation method was as described in Example 5.

EXAMPLE 12

Determination of Properties of Polylactic Acid Foamed Materials

The modified polylactic acid particles obtained with twin-screw extruders in Examples 5 to 12 and Comparative Examples 1 to 4 were injection-molded into behavioral standard strands and tested for heat distortion temperature, and the test method was in accordance with GB/T 1634.2-04; The heat-resistant polylactic acid foamed materials obtained in Examples 4 to 11 and Comparative Examples 1 to 4 were subjected to density test using a foaming technique of a mixed gas of supercritical carbon dioxide and nitrogen, and the test method was in accordance with GB/T 4472-2011. The above characterization test results were shown in Table 1.

TABLE 1

| Test index | Example 5 | Example 6 | Example 7 | Example 8 | Example 9 | Example 10 |
|---|---|---|---|---|---|---|
| Material density (g/cm$^3$) | 0.11 | 0.12 | 0.13 | 0.16 | 0.13 | 0.13 |
| Heat distortion temperature (° C.) | 115 | 118 | 120 | 122 | 121 | 118 |

| Test index | Example 11 | Example 12 | Comparative example 1 | Comparative example 2 | Comparative example 3 | Comparative example 4 |
|---|---|---|---|---|---|---|
| Material density (g/cm$^3$) | 0.13 | 0.12 | 0.26 | 0.26 | 0.28 | 1.25 |
| Heat distortion temperature (° C.) | 112 | 120 | 110 | 106 | 115 | 54 |

As is clear from Table 1, Examples 4 to 11 are found to have superior foaming performance by comparing Examples 5 to 12 with Comparative Examples 1 to 4, particularly, Examples 4 to 11 exhibit a low sheet density and an excellent heat distortion temperature. On the one hand, under the action of ethylene bis-12-hydroxystearamide grafted glycidyl citrate (EBH-g-ECA), the melt strength of polylactic acid is greatly improved, thereby meeting the requirements of continuous foaming, and the crystallization speed is increased, thereby increasing the heat distortion temperature of the polylactic acid from 55° C. to 115° C. or higher; On the other hand, under the action of the co-blowing agent, the cell growth of the polylactic acid becomes controllable, finally a foamed material having a high foaming ratio and a low material density is obtained, and the surface of the sheet is uniform and not rough. Comparative Example 1 uses a chain extender (ADR4368C/CS, BASF AG) and (ethylene bis-12-hydroxystearamide EBH), and Comparative Example 2 uses a chain extender (ADR4368C/CS, BASF AG), (ethylene bis-12-hydroxystearamide EBH), and triglycidyl citrate, and the density of the foamed materials prepared by both Comparative Examples are relatively large; Comparative Example 3 does not relates to the use the co-blowing agent, and the surface of the foamed material is not uniform and relatively rough; Comparative Example 4 does not have the multifunctional auxiliary agent EBH-g-ECA prepared in the present invention, and the polylactic acid material could not be foam molded. It can be seen that a simple compound of a chain extender and a crystallization nucleating agent is difficult to obtain a polylactic acid foamed material having satisfactory properties.

In addition, the heat-resistant polylactic acid foamed material maintains the advantages of biodegradation of polylactic acid, and fully complies with the American ASTM D6400 and EU EN13432 degradation certification standards, which is of a great significance for alleviating the shortage of petroleum resources and solving white pollution. Therefore, this composite material fully meets the development needs of the green low-carbon economy and has a broad application space.

The invention claimed is:

1. A compound, having a structural formula shown in a Formula I:

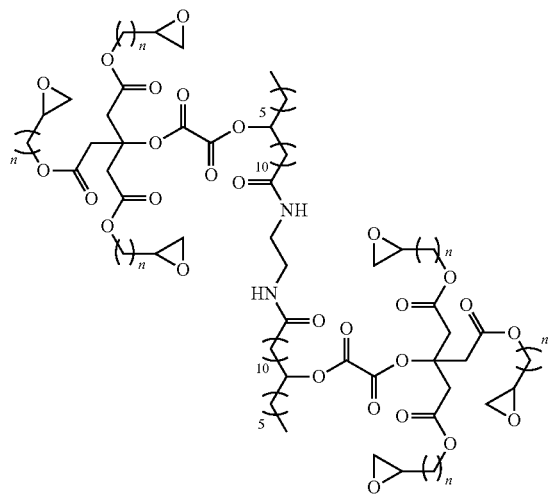

Formula I wherein n is an integer and $1 \le n \le 9$;

when n is 1, the structural Formula of the compound is as shown in a Formula Ia:

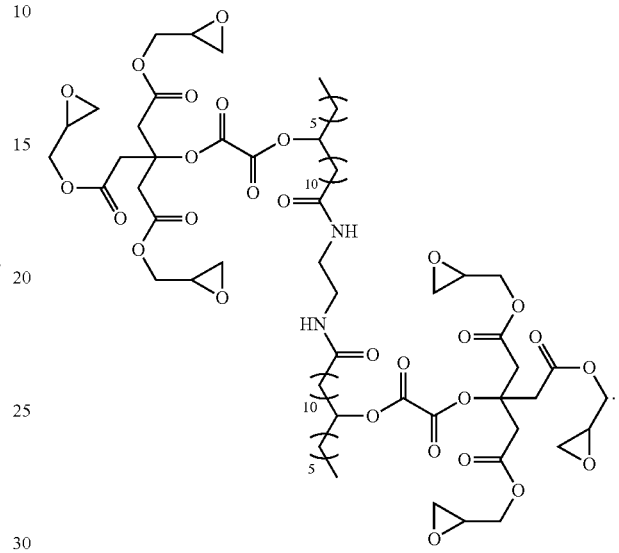

Formula Ia

2. A compound, having a structural formula shown in a Formula II:

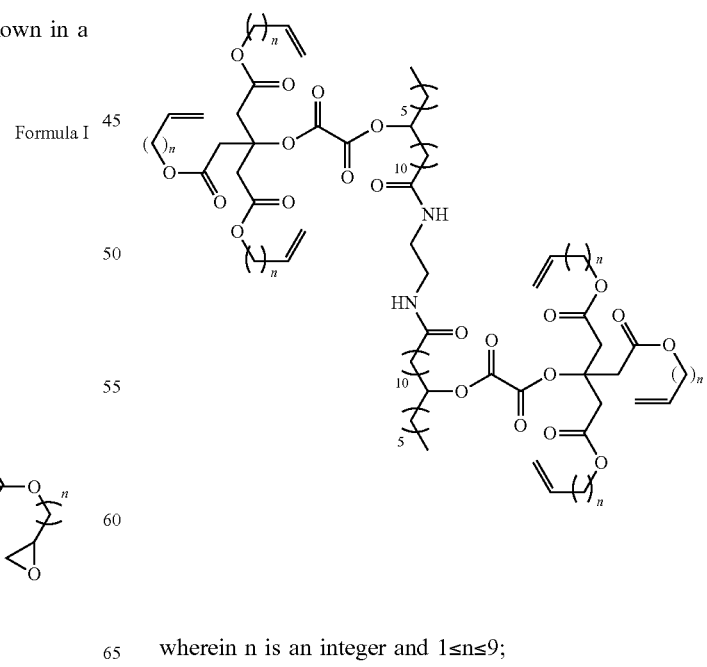

Formula II wherein n is an integer and $1 \le n \le 9$;

when n is 1, the structural Formula of the compound is as shown in a Formula IIa:

Formula IIa
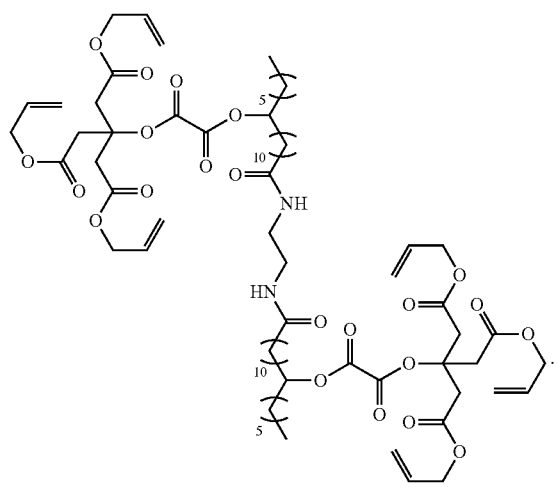
Formula III
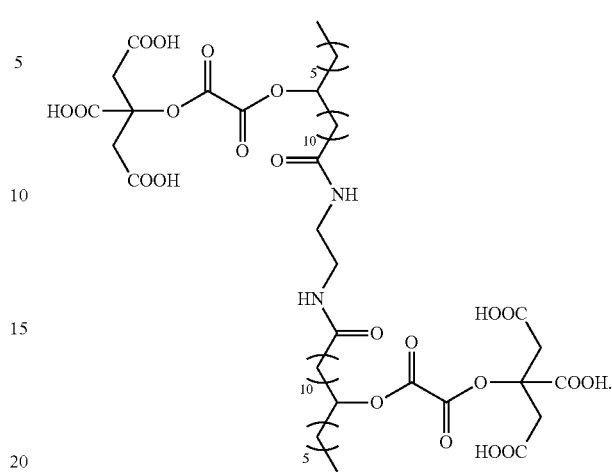
3. A compound, having a structural formula shown in a Formula III:
4. A method for preparing a first compound shown in a Formula I, comprising the following steps:

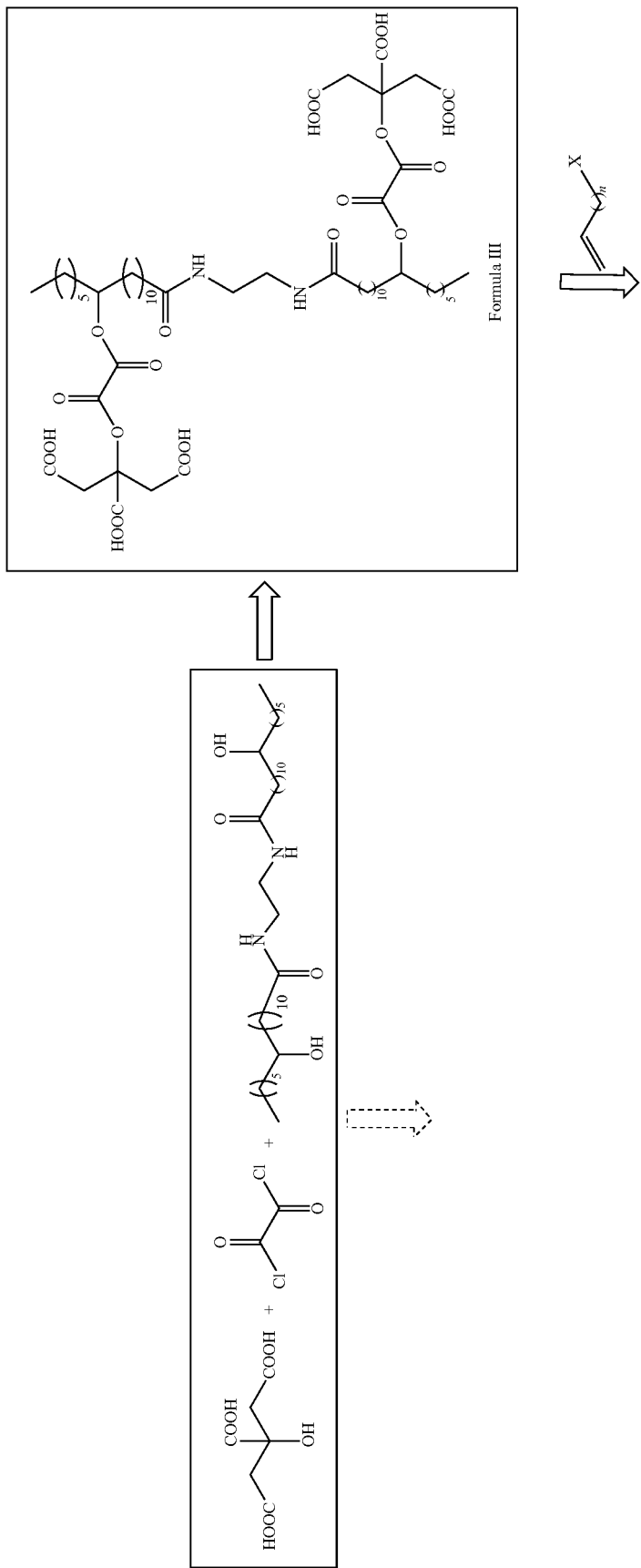

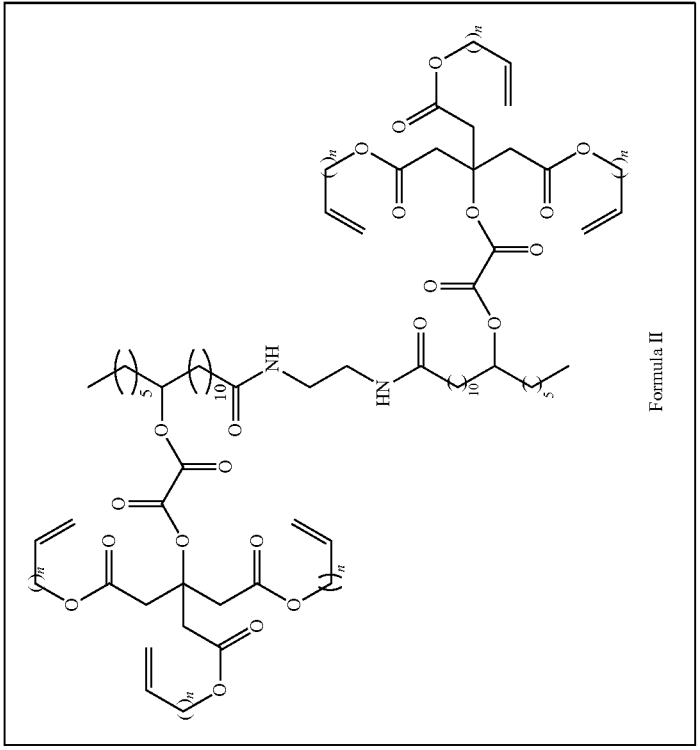
Formula II
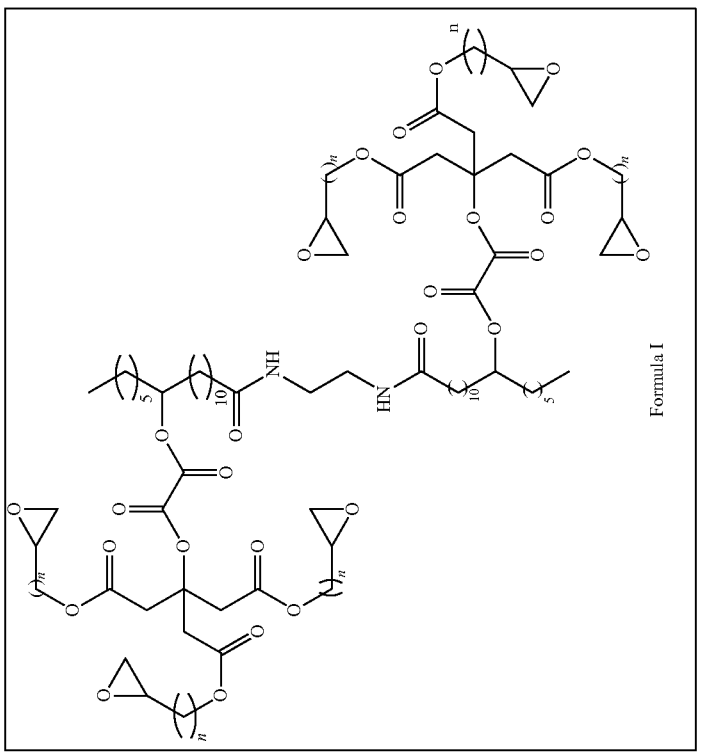
Formula I

S1: subjecting citric acid, oxalyl chloride and ethylene bis-12-hydroxystearamide to an elimination reaction to obtain ethylene bis-12-hydroxystearamide grafted citric acid of a Formula III;

S2: subjecting the ethylene bis-12-hydroxystearamide grafted citric acid of the Formula III obtained in step S1 and a halogenated olefin to an elimination reaction to obtain a compound shown in a Formula II;

S3: subjecting a second compound shown in the Formula II obtained in step S2 to an oxidation reaction to obtain the first compound shown in the Formula I;

wherein n is an integer and $1 \leq n \leq 9$.

5. The method according to claim 4, wherein when n is 1, a structural Formula of the Formula I is as shown in a Formula Ia, and a structural Formula of the Formula II is as shown in a Formula IIa; the method comprises the following steps:

S1a: uniformly mixing the citric acid, the oxalyl chloride, the ethylene bis-12-hydroxystearamide, a first catalyst with a first solvent, reacting by heating under a protection of an inert gas under stirring, and distilling under reduced pressure to obtain ethylene bis-12-hydroxystearamide grafted citric acid of the Formula III;

S2a: subjecting the ethylene bis-12-hydroxystearamide grafted citric acid of Formula III obtained in step S1a with the halogenated olefin, a second catalyst and a second solvent, reacting by heating under the protection of the inert gas under stirring, and washing and distilling under reduced pressure to obtain ethylene bis-12-hydroxystearamide grafted citric acid olefin ester of the Formula IIa;

S3a: uniformly mixing the ethylene bis-12-hydroxystearamide grafted citric acid olefin ester of the Formula IIa obtained in step S2a with a third catalyst and a third solvent, and reacting by heating, under the protection of the inert gas under stirring, and washing and distilling under the reduced pressure to obtain ethylene bis-12-hydroxystearamide grafted glycidyl citrate of the Formula Ia;

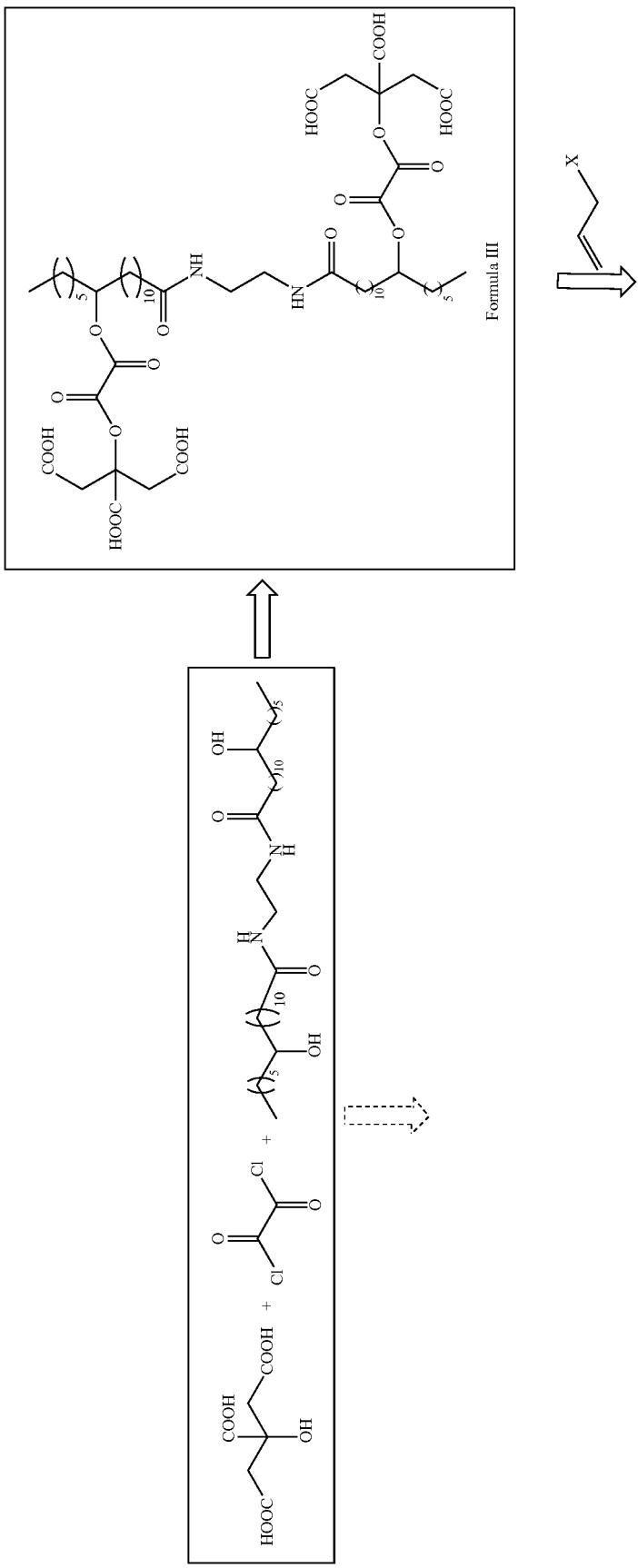

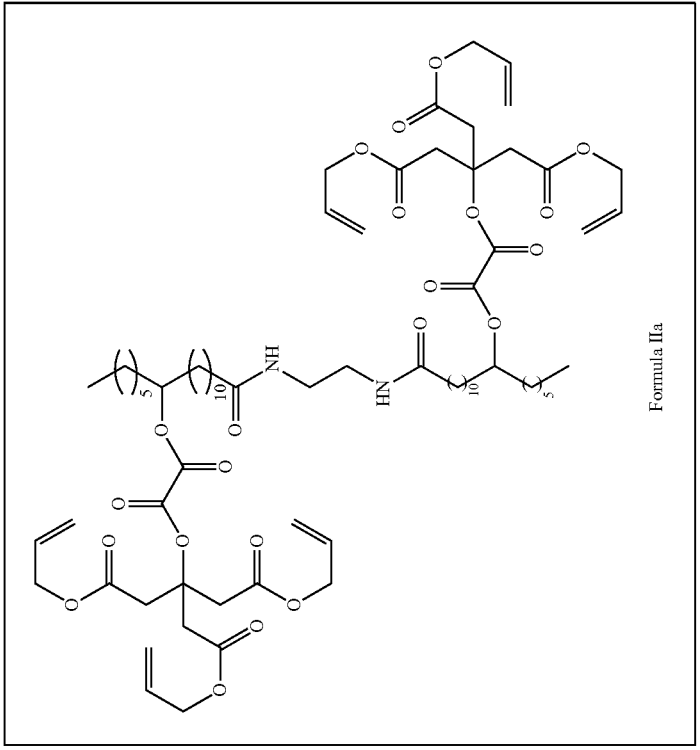
Formula IIa
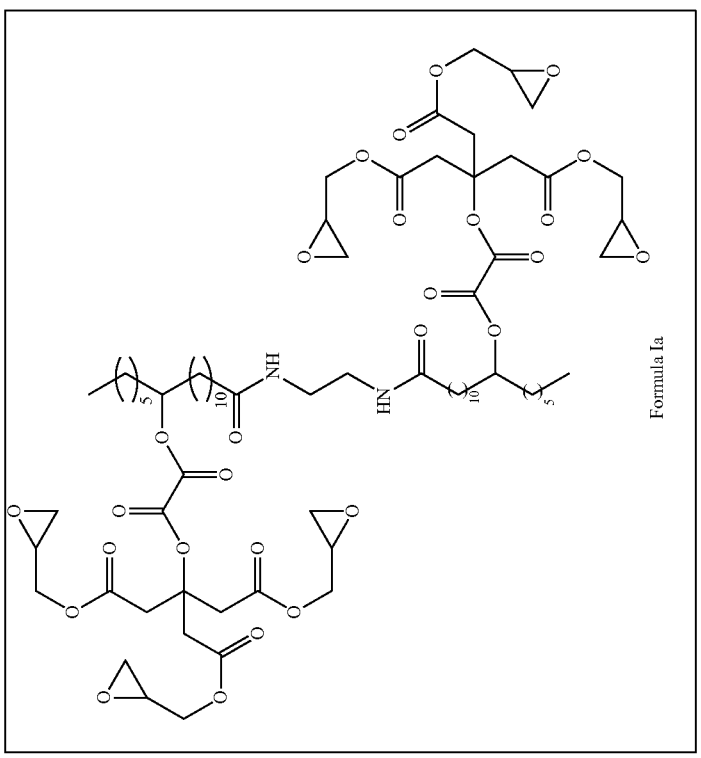
Formula Ia

6. The method according to claim 5, wherein
the first catalyst described in step S1a is at least one selected from the group consisting of potassium carbonate and sodium carbonate;
in the step S1a, the first solvent is at least one selected from the group consisting of chloroform, toluene and tetrahydrofuran;
in step S1a, conditions of reacting by heating are 20° C.-60° C., and 30-60 h;
in step S1a, a molar ratio of the citric acid, the oxalyl chloride, the ethylene bis-12-hydroxystearamide to the first catalyst is 2.2-2.5:2.2-2.5:1.0:3.0-5.5; a weight ratio of the ethylene bis-12-hydroxystearamide to the first solvent is 1:8-10;
in step S2a, the second catalyst is at least one of potassium carbonate and sodium carbonate;
in step S2a, the second solvent is at least one selected from the group consisting of dimethyl sulfoxide, N,N-dimethylformamide, toluene, and N,N-dimethylacetamide;
the halogenated olefin in step S2a is one selected from the group consisting of 3-bromo-1 propylene, 4-bromo-1-butene, 5-bromo-1-pentene, 6-bromo-1-hexene, 7-bromo-1-heptene, 8-bromo-1-octene, 9-bromo-1 nonene, 3-chloro-1-propene, 4-chloro-1-butene, 5-chloro-1-pentene, 6-chloro-1-hexene, 7-chloro-1-heptene, 8-chloro-1-octene, 9-chloro-1 nonene;
in step S2a, conditions of reacting by heating are 40° C.-60° C., and 25-50 h;
in step S3a, the third catalyst is at least one selected from the group consisting of m-chloroperoxybenzoic acid, peroxybenzoic acid, and p-nitroperoxybenzoic acid;
in step S2a, a molar ratio of ethylene bis-12-hydroxystearamide grafted citric acid, halogenated olefin to the third catalyst is 1.0:7.3-9.6:2-6; a weight ratio of ethylene bis-12-hydroxystearamide grafted citric acid to the third solvent is 1:10-15;
in step S3a, the third solvent is at least one selected from the group consisting of dichloromethane, trichloromethane, acetone, butanone and toluene;
in step S3a, conditions of reacting by heating are a temperature increase of 40° C.-60° C., and 20 h-50 h;
in step S3a, a molar ratio of ethylene bis-12-hydroxystearamide grafted citric acid olefin ester to the third catalyst is 1.0:6.6-8.5; a weight ratio of ethylene bis-12-hydroxystearamide grafted citric acid olefin ester to the third solvent is 1:8-13;
in the steps S1a, S2a, and S3a, the inert gas is nitrogen.

7. A polylactic acid foamed material, comprising the ethylene bis-12-hydroxystearamide grafted glycidyl citrate of the Formula Ia according to claim 1 and polylactic acid; the polylactic acid foamed material comprises the following components in weight percentage:

| | |
|---|---|
| the polylactic acid | 90-95% |
| a PBAT resin | 1-5% |
| a cell nucleating agent | 0.1-3% |
| a co-blowing agent | 0.1-3% |
| the ethylene bis-12-hydroxystearamide grafted glycidyl citrate | 0.1%-2.0%. |

8. The polylactic acid foamed material according to claim 7, wherein
The polylactic acid is at least one selected from the group consisting of L-type polylactic acid, D-type polylactic acid, and LD-mixed type polylactic acid;
the polylactic acid has a weight average molecular weight of 100,000 to 300,000 and a molecular weight distribution Mw/Mn of 1.3 to 1.8;
the PBAT resin is a copolymer of butylene adipate and butylene terephthalate;
the PBAT resin has a weight average molecular weight of 50,000-80,000 and a molecular weight distribution Mw/Mn of 1.2-1.6;
the cell nucleating agent is at least one selected from the group consisting of talcum powder, nano mica, and nano organic montmorillonite;
the co-blowing agent is at least one selected from the group consisting of a citric acid fatty acid glyceride, a polyoxyethylene sorbitan fatty acid ester, a sorbitan fatty acid, and a castor oil polyoxyethylene ether.

9. A method for preparing the polylactic acid foamed material according to claim 7, comprising the following steps:
(1) drying the polylactic acid with a high-speed mixer at 100° C.-110° C. for 20-40 min, adding the PBAT resin, the cell nucleating agent, the co-blowing agent, and the ethylene bis-12-hydroxystearamide grafted glycidyl citrate, mixing uniformly to obtain mixed materials, adding the mixed materials to a twin-screw extruder, performing melt-blending, stranding, air-cooling, and pelletizing to obtain modified polylactic acid particles, and packing under vacuum; wherein a length to diameter ratio of screws in the twin-screw extruder is 36:1-48:1, and a melt blending temperature is from 180° C. to 200° C.;
(2) adding the modified polylactic acid particles obtained in the step (1) to a twin-screw material forming machine, and performing melt-blending and extruding with a physical blowing agent to obtain a heat-resistant polylactic acid foamed material with a foaming ratio of 10-20;
the physical blowing agent in the step (2) is at least one selected from the group consisting of more of carbon dioxide, nitrogen, pentane, butane and Freon; a volume ratio of carbon dioxide to nitrogen is 20%:80%.

10. The method according to claim 9, wherein
the polylactic acid is one or a combination selected from the group consisting of more of L-type polylactic acid, D-type polylactic acid, and LD-mixed type polylactic acid;
the polylactic acid has a weight average molecular weight of 100,000 to 300,000 and a molecular weight distribution Mw/Mn of 1.3 to 1.8;
the PBAT resin is a copolymer of butylene adipate and butylene terephthalate;
the PBAT resin has a weight average molecular weight of 50,000-80,000 and a molecular weight distribution Mw/Mn of 1.2-1.6;
the cell nucleating agent is at least one selected from the group consisting of more of talcum powder, nano mica, and nano organic montmorillonite;
the co-blowing agent is at least one selected from the group consisting of more of a citric acid fatty acid glyceride, a polyoxyethylene sorbitan fatty acid ester, a sorbitan fatty acid, and a castor oil polyoxyethylene ether.

* * * * *